US010092192B2

(12) United States Patent
Lashkari et al.

(10) Patent No.: US 10,092,192 B2
(45) Date of Patent: Oct. 9, 2018

(54) METHODS FOR GENERATING MULTIPLE MISMATCHED CODED EXCITATION SIGNALS

(71) Applicants: Bahman Lashkari, Richmond Hill (CA); Andreas Mandelis, Scarborough (CA); Kaicheng Zhang, Toronto (CA)

(72) Inventors: Bahman Lashkari, Richmond Hill (CA); Andreas Mandelis, Scarborough (CA); Kaicheng Zhang, Toronto (CA)

( * ) Notice: Subject to any disclaimer, the term of this patent is extended or adjusted under 35 U.S.C. 154(b) by 448 days.

(21) Appl. No.: 14/979,797

(22) Filed: Dec. 28, 2015

(65) Prior Publication Data
US 2016/0213258 A1    Jul. 28, 2016

Related U.S. Application Data

(60) Provisional application No. 62/096,789, filed on Dec. 24, 2014.

(51) Int. Cl.
*A61B 5/00* (2006.01)
*G01S 15/89* (2006.01)
(Continued)

(52) U.S. Cl.
CPC .......... *A61B 5/0095* (2013.01); *A61B 5/7228* (2013.01); *A61B 5/7246* (2013.01);
(Continued)

(58) Field of Classification Search
CPC .... A61B 5/0095; A61B 5/7228; A61B 5/7246
See application file for complete search history.

(56) References Cited

U.S. PATENT DOCUMENTS

| 4,817,434 A | 4/1989 | Anderson |
|---|---|---|
| 6,048,315 A | 4/2000 | Chiao |

(Continued)

FOREIGN PATENT DOCUMENTS

| CN | 102764142 A | 11/2012 |
|---|---|---|
| WO | 2005104474 A8 | 11/2005 |

OTHER PUBLICATIONS

Behar, V., and, Adam, D., "Optimization of sparse synthetic transmit aperture imaging with coded excitation and frequency division". Ultrasonics. 2005; 43: 777-788.

(Continued)

*Primary Examiner* — Joseph M Santos Rodriguez
(74) *Attorney, Agent, or Firm* — Hill & Schumacher

(57) ABSTRACT

The present disclosure provides systems and methods for imaging based on the generation and use of mismatched coded excitation signals. Cross-correlation properties of the received signal reveal the location and/or timing and/or properties of the source. The use of mismatched signals enables spatial and/or temporal and/or functional encoding of the transmitted signals. In some embodiments, high-speed imaging may be performed by employing mismatched codes for spatial and/or temporal encoding, and by employing a subset of transducer elements as transmitters, and another subset of elements as receivers. Various example embodiments of different types of mismatched codes are provided, including codes that employ multiple frequency chirps, codes that employ concatenated multi-frequency binary phase-coded waveforms, and chirped binary phase-coded waveforms.

40 Claims, 25 Drawing Sheets

(51) Int. Cl.

| | |
|---|---|
| A61B 5/05 | (2006.01) |
| A61B 5/055 | (2006.01) |
| A61B 8/00 | (2006.01) |
| A61B 8/12 | (2006.01) |
| A61B 8/08 | (2006.01) |

(52) U.S. Cl.
CPC ...... *G01S 15/8913* (2013.01); *G01S 15/8915* (2013.01); *G01S 15/8922* (2013.01); *G01S 15/8961* (2013.01); *A61B 5/0033* (2013.01); *A61B 5/055* (2013.01); *A61B 5/0507* (2013.01); *A61B 8/12* (2013.01); *A61B 8/4494* (2013.01); *A61B 8/5207* (2013.01); *A61B 2576/00* (2013.01)

(56) References Cited

U.S. PATENT DOCUMENTS

| | | |
|---|---|---|
| 6,547,733 B2 | 4/2003 | Hwang |
| 7,066,886 B2 | 6/2006 | Song |
| 7,627,054 B2 | 12/2009 | Diaz Fuente |
| 8,939,909 B2 | 1/2015 | Wegner |
| 2005/0008065 A1 | 1/2005 | Schilling |
| 2006/0241454 A1 | 10/2006 | Ustuner |
| 2007/0239002 A1 | 10/2007 | Alam |
| 2011/0213234 A1 | 9/2011 | Leskiw |

OTHER PUBLICATIONS

Bredthauer, G.R. and, von Ramm, O.T., "Array design for ultrasound imaging with simultaneous beams". In IEEE Int. Symp. Biomedical Imaging; 2002; Washington D.C.

Chiao, R.Y., Thomas, L.J. and, Silverstein, S.D., "Sparse array imaging with spatially-encoded transmits". IEEE Ultrasonics Symposium. 1997; 2: 1679-1682.

Chiao, R.Y., and, Thomas, L.J., "Synthetic transmit aperture imaging using orthogonal Golay coded excitation". Proc. IEEE Ultrason. Symp. 2000; 1677-1680.

Cook, C.E., "linear FM signal formats for beacon and communication systems," IEEE Trans. Aerosp. Electron. Syst., vol. AES-10, No. 4 , pp. 471-478, 1974.

El-Khamy, S.E., Shaaban, S.E., and Thabet, E.A., "Efficient multiple access communications using multi-user chirp modulation signals". IEEE 4th International Conference on Spread-Spectrum Systems and Techniques (ISSSTA\'96). 1996; 1209-1213.

El-Khamy, S.E., Shaaban, S.E., and Thabet, E.A., "Frequency-hopped multi-user chirp modulation (FH/M-CM) for multipath fading channels". Proceedings of the Sixteenth National Radio Science Conference, NRSC '99. 1999: C6/1-C6/8.

Golay, M., "Complementary Series," IRE Trans Inf Theory, vols. IT-7:82-87, 1961.

Gran, F., and, Jensen, J.A., "Multi element synthetic aperture transmission using a frequency division approach". IEEE Ultrasonic Symposium. 2003; 1942-1946.

Gran, F., and, Jensen, J.A., "Spatio-temporal encoding using narrow-band linear frequency modulated signals in synthetic ultrasound imaging". SPIE Proc. Progress in Biomedical Optics and Imaging. 2005; 5750: 405-416.

Gran, F., and, Jensen, J.A., "Frequency division transmission imaging and synthetic aperture reconstruction". IEEE Trans. Ultrason. Ferroelectr. Freq. Control. 2006; 53(5): 900-911.

Griswold, M.A., Jakob, P.M., Chen, Q. , Goldfarb, J.W., Manning, W.J., Edelman, R.R. and Sodickson, D.K., "Resolution enhancement in single-shot imaging using simultaneous acquisition of spatial harmonics (SMASH)". Magn Reson Med. 1999; 41: 1236-1245.

Hergum, T., Bjastad, T., Kristoffersen, K., and Tarp, H., "Parallel beamforming using synthetic transmit beams". IEEE Trans. Ultrason. Ferroelectr. Freq. Control. 2007; 54(2): 271-280.

Jaffe, J.S., and, Cassereau, P.M., "Multibeam imaging using spatially variant insonification". J. Acoust. Soc. Am. 1988; 83(4): 1458-1464.

Jensen, J.A., Nikolov, S.I., Gammelmark, K.L., and Pedersen, M.H., "Synthetic Aperture Ultrasound Imaging". Ultrasonics J. 2006; 44: p. e5-e15.

Karaman, M., Li, P.-C., and O'Donnell, M., "Synthetic aperture imaging for small scale systems". IEEE Trans. Ultrason. Ferroelectr. Freq. Control. 1995; 42: 429-442.

Kiymik, M.K., Güler, I., Hasekioglub, O., Karaman, M., "Ultrasound imaging based on multiple beamforming with coded excitation". Signal Processing. 1997; 58: 107-113.

Lee, B.B., and, Furgason E.S., "Golay Codes for Simultaneous Multi-Mode Operation in Phased Arrays". Ultrasonics Symposium. 1982; 821-825.

Madore, B., White, P.J., Thomenius, K., and, Clement, T. "Accelerated focused ultrasound imaging". IEEE Trans. Ultrason. Ferroelectr. Freq. Control. 2009; 56(12): 2612-2623.

Mallart, R., Fink, M., "Improved imaging rate through simultaneous transmission of several ultrasound beams". Proc. SPIE 1730, New Developments in Ultrasonic Transducers and Transducer Systems. 1992; 120-130.

Mienkina, M.P., Friedrich, C.S., Gerhardt, N.C., Beckmann, M.F., Schiffner, M.F., Hofmann, M.R., Schmitz, G., "Multispectral Photoacoustic Coded Excitation imaging using unipolar Orthogonal Golay Codes," Optics Express, 2010; 18(9): 9076-9087.

Misaridis, T. and, Jensen J.A., "Space-time encoding for high frame rate ultrasound imaging". Ultrasonics. 2002; 40: 593-597.

Misaridis T. and, Jensen J.A., Use of modulated excitation signals in medical ultrasound, Part III: High frame rate imaging. IEEE Trans. Ultrason., Ferroelect., Freq. Contr. 2005: 52(2), 207-218.

Montaldo, G., Tanter, M., Bercoff, J., Benech, N., Fink, M., "Coherent Plane-Wave Compounding for Very High Frame Rate Ultrasonography and Transient Elastography". IEEE Trans. Ultrason. Ferr. Freq. Contr. 2009; 56(3): 489-506.

Purdy, D.S. "In orbit active array calibration for NASA's LightSAR". IEEE Proceedings of the Radar Conference. 1999; 172-176.

Sakamoto, T., and, Sato. T., "Code-Division Multiple Transmission for High-Speed UWB Radar Imaging With an Antenna Array". IEEE Transactions on Geoscience and Remote Sensing. 2009; 47(4): 1179-1186.

Shattuck, D.P., Weinshenker, M.D., Smith, S.W., and, von Ramm, O.T., "Explososcan: A parallel processing technique for high speed ultrasound imaging with linear phased arrays". J. Acoust. Soc. Am. 1984; 75(4): 1273-1282.

Shen, J., and Ebbini, E.S., "A new coded-excitation ultrasound imaging system—Part I: Basic principles". IEEE Trans. Ultrason. Ferroelectr. Freq. Control. 1996; 43: 131-140.

Silverstein, S.D., "Application of orthogonal codes to the calibration of active phased array antennas for communications satellites". IEEE Trans. Sig. Proc. 1997; 45(1): 206-218.

Tanter, M., and Fink, M. "Ultrafast Imaging in Biomedical Ultrasound". IEEE Trans. Ultrason. Ferroelectr. Freq. Control. 2014; 61(1): 102-119.

Von Ramm, O.T., Smith, S.W., and, Pavy, H.G., "High-speed ultrasound volumetric imaging system—Part II: Parallel processing and image display". IEEE Trans. Ultrason. Ferroelectr. Freq. Control. 1991; 38(2): 109-115.

Yang, M., and, Chakrabarti, C., "Design of orthogonal coded excitation for synthetic aperture imaging in ultrasound systems". IEEE International Symposium on Circuits and Systems (ISCAS). 2012; 113-116.

Kim, B.H., Song, T.K., "Multibeam Simultaneous Transmit Multizone (MB-STMZ) focusing method using modulated orthogonal codes for ultrasound imaging," Proc. SPIE, 2004; 5373: 315-323.

O'Donnell, M., Wang, Y., "Coded Excitation for Synthetic Aperture Ultrasound Imaging," IEEE Trans. Ultrason. Ferroelectr. Freq. Control., 2005; 52(2): 171-176.

| Transmitted Element | Sequential order of CEs transmitted every 150 μs | | | | | | | | |
|---|---|---|---|---|---|---|---|---|---|
| #1 | FM1 | FM2 | FM3 | FM7* | FM4 | FM3 | FM2 | FM1 | FM4 | FM7 |
| #2 | FM3 | FM3* | FM1 | FM2 | FM3 | FM2 | FM4 | FM7 | FM2* | FM1 |
| #3 | FM4 | FM1 | FM4 | FM3 | FM1 | FM7* | FM1 | FM3 | FM3* | FM2 |
| #4 | FM2 | FM4 | FM7 | FM4* | FM7 | FM1 | FM3 | FM2 | FM1 | FM3 |

"*" indicates phase shift by 180°.

FIG. 17A

| GCs | Complementary elements of the GC |
|---|---|
| 1-bit | [1] & [1] |
| 2-bit | [1,1] & [1,-1] |
| 4-bit | [1,1,-1,1] & [1,1,1,-1] |
| 10-bit | [1,1,-1,1,-1,1,-1,-1,1,1] & [1,1,-1,1,1,1,1,1,-1,-1] |

FIG. 17B

| Transmitted Element | Sequential order of Combined GC-FMs transmitted every 150μs | | | | | | | | |
|---|---|---|---|---|---|---|---|---|---|
| | The first part of complementary GCs | | | | | The second part of complementary GCs | | | | |
| #1 | CGC1 | CGC2 | CGC4 | CGC10ʳ | CGC4 | CGC1 | CGC2 | CGC4 | CGC10ʳ | CGC4 |
| #2 | CGC10ʳ | CGC1 | CGC2ʳ | CGC4 | CGC2ʳ | CGC10ʳ | CGC1 | CGC2ʳ | CGC4 | CGC2ʳ |
| #3 | CGC2 | CGC4 | CGC10ʳ | CGC1 | CGC1* | CGC2 | CGC4 | CGC10ʳ | CGC1 | CGC1* |
| #4 | CGC4 | CGC10ʳ | CGC1 | CGC2ʳ | CGC10ʳ | CGC4 | CGC10ʳ | CGC1 | CGC2ʳ | CGC10ʳ |

"ʳ" indicates employing reverse chirp.
"*" indicates phase shift by 180°.

METHODS FOR GENERATING MULTIPLE MISMATCHED CODED EXCITATION SIGNALS

CROSS-REFERENCE TO RELATED APPLICATION

This application claims priority to U.S. Provisional Application No. 62/096,789, titled "METHODS FOR GENERATING MULTIPLE MISMATCHED CODED EXCITATION SIGNALS" and filed on Dec. 24, 2014, the entire contents of which is incorporated herein by reference.

BACKGROUND

The present disclosure relates to systems and methods of imaging. More particularly, the present disclosure relates to systems and methods of imaging that employ coded excitation with mismatched codes.

In the field of biomedical ultrasound (ultrasound) imaging, in which phased array transducers with several elements are used for transmission and detection of ultrasound signal, different approaches have been proposed to achieve high-frame-rate ultrasound imaging while preserving image quality. Parallel beamforming or multi-line transmission is a method based on generating a spherical wave by transmitting a diverging beam from multiple elements, which is also called "explososcan" (Shattuck, et. al J. Acoust. Soc. Am. 1984; 75(4): 1273-1282) (von Ramm, et al., IEEE Trans. Ultrason. Ferroelectr. Freq. Control. 1991; 38(2): 109-115) (Hergum, et. al, IEEE Trans. Ultrason. Ferroelectr. Freq. Control. 2007; 54(2): 271-280) (Madore, et. al, IEEE Trans. Ultrason. Ferroelectr. Freq. Control. 2009; 56(12): 2612-2623).

Similarly, there were attempts to perform fast volumetric ultrasound imaging by multiple beams (Bredthauer and von Ramm, IEEE Int. Symp. Biomedical Imaging; 2002). The complexity of those systems was fairly high, however, they enabled 3D imaging. Parallel beamforming can also be used to generate a plane wave beam. Plane-wave compounding is shown to be an effective method for high-frame-rate imaging (Montaldo, et. al, IEEE Trans. Ultrason. Ferr. Freq. Contr. 2009; 56(3): 489-506) (Mallart and Fink, Proc. SPIE 1730, 1992: 120-130) (Tanter and Fink, IEEE Trans. Ultrason. Ferroelectr. Freq. Control. 2014; 61(1): 102-119).

Another promising method is multiple-element synthetic aperture imaging (SAI) which can increase the frame rate while reducing system complexity (Jensen, et. al, Ultrasonics J. 2006; 44: e5-e15) (Karaman, et. al, IEEE Trans. Ultrason. Ferroelectr. Freq. Control. 1995; 42: 429-442). Many different techniques have been employed to perform multiple transmissions in the SAI method with combination of coded excitations.

There are two main types of coded excitations, frequency-coded and phase-coded signals. The most popular frequency-coding is linear frequency modulation, and examples of phase-coding are Golay codes and Barker codes. One common technique was based on choosing long independent Golay codes (Golay Code) or m-sequences, to minimize the cross-correlation (cross-correlation) between the signals (Kiymik, et. al, Signal Processing. 1997; 58: 107-113) (Shen and Ebbini, IEEE Trans. Ultrason. Ferroelectr. Freq. Control. 1996; 43: p. 131-140). It was also shown that, by employing the equivalence properties of Golay Codes, a set of Golay Codes can be generated in a way that while their cross-correlations are nonzero, the summation of cross-correlations of complementary codes cancels each other out (Lee and Furgason, Ultrasonics Symposium. 1982: 821-825). The same technique was also used for multiple-spectral photoacoustic imaging (Mienkina et al., Optics Express, 2010; 18(9): 9076-9087). The other techniques employed the Hadamard decoding method (Chiao, et. al, IEEE Ultrasonics Symposium. 1997; 2: 1679-1682.) or a combination of Hadamard decoding and dissimilar Golay Codes (ultrasound U.S. Pat. No. 6,048,315, 2000) (Chiao and Thomas, Proc. IEEE Ultrason. Symp. 2000: 1677-1680). Hadamard decoding has been widely used to generate orthogonal codes with Golay Codes (Yang et. al, IEEE International Symposium on Circuits and Systems (ISCAS). 2012: 113-116).

Various methods have been suggested to generate mismatched codes with frequency modulation (FM) signals as well. Misaridis and Jensen have suggested employing two chirps with similar duration and bandwidth but with opposite slopes, however the method is limited to only two codes and therefore fails to be practical in many applications (Misaridis and Jensen, IEEE Trans. Ultrason., Ferroelect., Freq. Contr. 2005:52(2), 207-218).

Other methods that have been employed to generate multiple mismatched codes are either dissimilar durations among different codes, or dissimilar frequency ranges among different codes (the frequency ranges of the different codes may overlap but cannot be identical). A linear frequency sweep per each of dissimilar frequency ranges or per each of dissimilar durations produces a frequency slope different from others. However, the disadvantage is that each of those unique frequency modulations also has a unique signal-to-noise ratio (SNR) and resolution. It should be clarified that the frequency sweeps employed in these other methods consist of only one linear frequency sweep per code (see FIG. 16A). Therefore, the durations mentioned above refer to total frequency code length (i.e. there is no sub-chirp) (Misaridis, and, Jensen, IEEE Trans. Ultrason., Ferroelect., Freq. Contr. 2005: 52(2), 207-218.). Therefore, these methods result in non-uniform signal-to-noise ratios (SNR) and resolutions.

Hadamard decoding has also been employed with up- and down-sweep chirps to generate a set of orthogonal codes (Misaridis and Jensen, Ultrasonics. 2002; 40: 593-597).

Alternatively, the bandwidth can be divided into several parts, so that, multiple excitation signals cover different parts of the bandwidth. The excitations can be single frequency waveforms or chirps (Gran and Jensen, SPIE Proc. 2005; 5750: 405-416) (Grant and Jensen, IEEE Ultrasonic Symposium. 2003: 1942-1946) (Behar and Adam, Ultrasonics. 2005; 43: 777-788). The combination of frequency spectrum dividing and opposite slopes has also been proposed to generate multiple focal points by simultaneous multiple transmissions (ultrasound U.S. Pat. No. 7,066,886 B2).

It should be added that very similar methods have been employed in other fields such as radar, sonar, and even wireless communications. These methods are readily applicable to biomedical ultrasound imaging. A proposed method for sonar multibeam imaging is frequency hopping (Jaffe and Cassereau, J. Acoust. Soc. Am. 1988; 83(4): 1458-1464). The bandwidth is divided into a number of individual frequencies; then, these frequencies are distributed distinctively using a frequency hopping code to produce uncorrelated waveforms. Using long mismatched pseudonoise (PN) sequences has also been suggested for multiple transmission radar imaging (Sakamoto and Sato, IEEE Transactions on Geoscience and Remote Sensing. 2009; 47(4): 1179-1186.). The Hadamard encoding technique has been extensively employed in communication phase array antennas (Silverstein, IEEE Trans. Sig. Proc. 1997; 45(1): 206-218) (Purdy, IEEE Proceedings of the Radar Conference. 1999: 172-176). Also, methods similar to parallel beamforming has been employed in MRI (Griswold, et. al, Magn Reson Med. 1999; 41: 1236-1245).

A related scheme was suggested by El-Khamy et al. (El-Khamy, et. al, IEEE 4th International Conference on Spread-Spectrum Systems and Techniques, 1996; 1209-1213) (El-Khamy, et. al, Proceedings of the Sixteenth National Radio Science Conference, NRSC '99. 1999; C6/1-C6/8). These authors divided the chirp duration into two halves, each having a separate and non-overlapping bandwidth, and swept the frequency range with two different slopes to obtain identical time and bandwidth. It should be clarified that the frequency range has been swept only once in this method but with two different slopes in the two parts of the bandwidth (e.g., as shown in FIG. 16B). The drawback of this method is that the frequency sweeps are nonlinear and non-uniform, and therefore the method fails to generate uniform signal-to-noise ratio and resolution. The advantage, on the other hand, is that there is no limitation in the number of the possible mismatched codes.

Another attempt to increase the lateral resolution without sacrificing the frame rate was through "multi-beam simultaneous multi-zone focusing method" (Kim and Song, Proc. SPIE, 2004; 5373, 315-323) (Hwang and Song, U.S. Pat. No. 6,547,733 B2, 2003). This method was implemented by combining M orthogonal GCs with L orthogonal chirps to obtain M scan lines; each consists of L different focusing depths. The orthogonal GCs had a similar number of bits and selected as described by Chiao and Thomas (Chiao and Thomas, Proc. IEEE Ultrason. Symp. 2000: 1677-1680). The orthogonal chirps were generated by dividing the frequency bandwidth of the transducer. Examples were presented for the case M=L=2 (Kim and Song, Proc. SPIE, 2004; 5373, 315-323).

To prevent the mixing of group signals, Cook suggested the use of V-FM signals (C. E. Cook, IEEE Trans. Aerosp. Electron. Syst., 1974: 10(4), 471-478). When for instance beacon codes can be transmitted; the first arm of the V-FM can be used to transmit the synchronization signal and the second arm for the message signal. It is similar to transmitting two LFM chirps with different slopes where the first slope (down-chirp) identifies the type of the message (e.g. altitude, heading, etc.) and the second LFM (up-chirp) for the data.

SUMMARY

The present disclosure provides systems and methods for imaging based on the generation and use of mismatched coded excitation signals. Cross-correlation properties of the received signal reveal the location and/or timing and/or properties of the source. The use of mismatched signals enables spatial and/or temporal and/or functional encoding of the transmitted signals. In some embodiments, high-speed imaging may be performed by employing mismatched codes for spatial and/or temporal encoding, and by employing a subset of transducer elements as transmitters, and another subset of elements as receivers. Various example embodiments of different types of mismatched codes are provided, including codes that employ multiple frequency chirps, codes that employ concatenated multi-frequency binary phase-coded waveforms, and chirped binary phase-coded waveforms.

Accordingly, in a first aspect, there is provided a method of performing encoded imaging using mismatched coded waveforms, the method comprising:
  a) transmitting coded imaging energy with one or more transmitter elements such that the coded imaging energy is directed onto an object to be imaged, wherein the coded imaging energy comprises a plurality of mismatched coded waveforms that are encoded with mismatched codes;
  b) receiving, with an array of receiver elements, secondary energy that is responsively generated, reflected or transmitted by the object, and thereby obtaining a set of received signals;
  c) calculating cross-correlations of the set of received signals with the plurality of mismatched coded waveforms, such that the cross-correlations isolate a contribution of each mismatched coded waveform to the set of received signals; and
  d) processing the cross-correlations to generate an image;
  wherein each coded mismatched waveform comprises a series of time divisions, each time division comprising a chirp;
  wherein the slope of each chirp, in each time division of each mismatched coded waveform, is unique; and
  wherein each mismatched coded waveform has an associated frequency range, such that the frequency ranges of the mismatched coded waveforms overlap at least in part.

In another aspect, there is provided a method of performing encoded imaging, the method comprising:
  a) transmitting coded imaging energy with one or more transmitter elements such that the coded imaging energy is directed onto an object to be imaged, wherein the coded imaging energy comprises a plurality of mismatched coded waveforms that are encoded with mismatched codes;
  b) receiving, with an array of receiver elements, secondary energy that is responsively generated, reflected or transmitted by the object, and thereby obtaining a set of received signals;
  c) calculating cross-correlations of the set of received signals with the plurality of mismatched coded waveforms, such that the cross-correlations isolate a contribution of each mismatched coded waveform to the set of received signals; and
  d) processing the cross-correlations to generate an image;
  wherein the plurality of mismatched coded waveforms comprise two or more concatenated mismatched coded waveforms, wherein each concatenated mismatched coded waveform is formed by concatenating two or more phase-coded waveforms having different frequencies.

In another aspect, there is provided a method of performing encoded imaging, the method comprising:
  a) transmitting coded imaging energy with one or more transmitter elements such that the coded imaging energy is directed onto an object to be imaged, wherein the coded imaging energy comprises a plurality of mismatched coded waveforms that are encoded with mismatched codes;
  b) receiving, with an array of receiver elements, secondary energy that is responsively generated, reflected or transmitted by the object, and thereby obtaining a set of received signals;
  c) calculating cross-correlations of the set of received signals with the plurality of mismatched coded waveforms, such that the cross-correlations isolate a contribution of each mismatched coded waveform to the set of received signals; and d) processing the cross-correlations to generate an image;
wherein the plurality of mismatched coded waveforms are two or more phase-coded waveforms, wherein each bit of each phase-coded waveform is chirped;
wherein the chirps within a given phase-coded waveform are equal; and
wherein the chirps among different phased-coded waveforms are different; and
wherein each phase-coded waveform has an associated frequency range, such that the frequency ranges of the phase-coded waveforms overlap at least in part.

In another aspect, there is provided a method of performing encoded imaging using mismatched coded waveforms, the method comprising:

a) transmitting coded imaging energy with one or more transmitter elements such that the coded imaging energy is directed onto an object to be imaged, wherein the coded imaging energy comprises a plurality of mismatched coded waveforms that are encoded with mismatched codes, wherein the one or more transmitter elements are an array of transmitter elements, and wherein the coded imaging energy emitted from each transmitter element is spatially and temporally coded, such that each transmitter element emits a unique series of mismatched coded waveforms;

b) receiving, with an array of receiver elements, secondary energy that is responsively generated, reflected or transmitted by the object, and thereby obtaining a set of received signals, wherein the array of transmitter elements and the array of receiver elements are elements of a transducer array, such that a first subset of elements of transducer array are configured as transmitters, and a second subset of elements of the transducer array are configured as receivers;

c) calculating cross-correlations of the set of received signals with the plurality of mismatched coded waveforms, such that the cross-correlations isolate a contribution of each mismatched coded waveform to the set of received signals; and d) processing the cross-correlations to generate a first image; and e) performing the following steps one or more times:
    selecting different subsets of the elements of the transducer array for the array of transmitter elements and the array of receiver elements; and
    repeating steps a) to d);
thereby obtaining one or more additional images.

A method of performing encoded imaging using mismatched coded waveforms, the method comprising:

a) transmitting coded optical imaging energy with one or more optical transmitter elements such that the coded optical imaging energy is directed onto an object to be imaged, wherein the coded optical imaging energy comprises a plurality of mismatched coded waveforms that are encoded with mismatched codes;

b) receiving, with an array of ultrasound receiver elements, secondary energy that is responsively generated by the object, and thereby obtaining a set of received signals;

c) calculating cross-correlations of the set of received signals with the plurality of mismatched coded waveforms, such that the cross-correlations isolate a contribution of each mismatched coded waveform to the set of received signals; and d) processing the cross-correlations to generate an image;
wherein the coded mismatched waveforms comprise frequency chirps having equal and opposite slopes.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 17A-C are tables describing (A) the sequence of ten frequency modulation signals transmitted every 150 μs from four elements simultaneously; (B) the Golay Codes (GC) used to generate combined GC-FM signals; and (C) the sequences of five combined GC-FM signals transmitted every 150 μs from four elements simultaneously. Also shown are, the complementary GCs transmitted after the first parts (second parts). It should be mentioned that the combined GC-FM codes used in this example (FIG. 15C), had identical total code length of 12 μs (e.g. FIGS. 11A and B), using the same bandwidth and dissimilar Golay code bit numbers, the slopes of the codes in different combined GC-FM codes were automatically different, therefore the codes were mismatched.

DETAILED DESCRIPTION

Figure 1A:
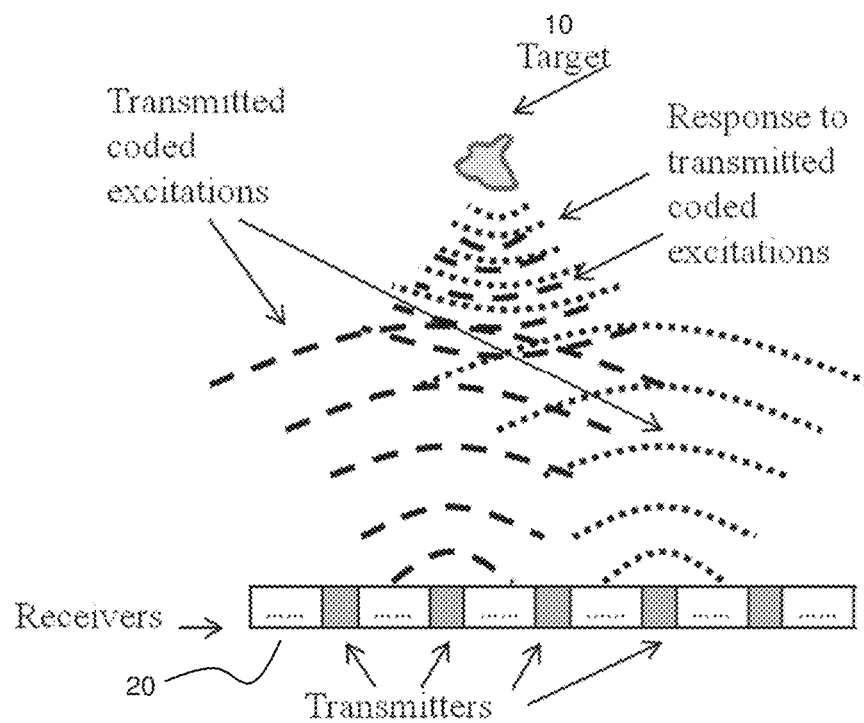
FIGS. 1A, 1B and 1C illustrate imaging using coded excitations with mismatched codes for (A) a single source that sequentially emits mismatching codes; (B) multiple sources that emit mismatching codes (spatial encoding); and (C) multiple sources that emit sequential mismatching codes (both temporal and special encoding together).

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

As used herein, the phrase "mismatched codes" and "coded waveforms" refers to a set of two or more waveforms that have a cross-correlation amplitude that is substantially less than their peak autocorrelation amplitudes. For example, in one embodiment, the maximum cross-correlation value of any two (mismatched) coded waveforms (codes) is less than 25% of the peak autocorrelation values, or less than 20% of the peak autocorrelation values, or less than 15% of the peak autocorrelation values, or less than 10% of the peak autocorrelation values, or less than 5% of the peak autocorrelation values, or less than 1% of the peak autocorrelation values.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

The present disclosure relates to systems and methods for generating mismatched coded excitation signals and their application in various fields, such as biomedical ultrasound, radar, sonar, nondestructive testing ultrasound, photoacoustics, MRI imaging, microwave imaging and communication systems.

Mismatched codes, as employed in the present disclosure, are signals with strong autocorrelation and very weak cross-correlations among themselves. One of the major uses of mismatched codes is in systems with array antennas or transmitter/receivers where multi-input and multi-output communication is required. The use of mismatched signals enables spatial and temporal encoding of the signals and thus facilitates applications that require multiple-output or fast successive signal transmissions. Mismatched codes can also be used for simultaneous functional encoding. Example methods provided herein are related to two types of coded excitation, frequency modulation signals (FM) and Golay codes (Golay, IRE Trans. Inf. Theory IT-7:82-87, 1961).

As described below, coded excitation methods can be employed for spatial encoding of excitation energy, temporal coding of excitation energy, or both spatial and temporal coding of excitation energy. The coded excitation energy is directed onto an object (e.g. a sample, structure, material, or patient). Energy that is responsively emitted or reflected from the object or transmitted (e.g. refracted) through the object is detected. The detected energy is then matched filtered to the set of mismatched codes, thereby allowing the components of the detected energy to be associated with the location from where the energy component was emitted, or the time at which the energy component was emitted.

Use of Mismatched Codes for Spatial Encoding

In some embodiments, mismatched coded excitations can be used to perform spatial encoding and decoding. In applications such as ultrasound array imaging, the interpretation of the detected signal relies on time-of-flight to estimate the location of the source of the signal response. If transmissions perform subsequently (one at a time) or via beamforming, it is possible to estimate the time that takes for the signal to reach the target and reflect (or scatter) to the receiver as the locations of the transmitter and receiver elements are known. Therefore, the location of the target relative to each detector element can be estimated. The use of mismatched codes enables the decoding of the received signals, thus, revealing the location of transmitted signals. Therefore, after discriminating different mismatched codes and identifying their transmission location, the signals can be dealt with as if they were independent transmission and detection events.

FIG. 1A shows a schematic example of spatial encoding using an array 20 of transducers (array elements may function as both as transmitters and receivers, or may be provided as separate transmitters and receivers). For simplicity, only two mismatched coded waveforms are shown. The transmitted signals generate corresponding responses that are emitted or reflected from the target, therefore each detecting element can discriminate the response of each code and by finding the source, the time-of-flight of the signal to the target and the receiver and therefore relative distance of the target can be estimated. The relative distances to several elements reveal the spatial location (or shape) of the target.

For example, for each transmitted signal, a set of cross-correlation signals will be generated (number of signals is the number of receiver elements; Nr). The location of each transmitter and receiver is known, therefore, the delay time shows the relative location of target (the round trip). Therefore, the total number of cross-correlation signals will be Nr×Nt (number of receiver elements by number of transmitters). For each set of received elements and on transmitter, one low resolution image can be generated. Afterwards, the low-resolution images can be superposed together to generate the high resolution image. Alternatively, the various cross-correlations can be processed to generate a single high-resolution image without generating intermediate low-resolution images.

This example method of spatially encoded signal processing is applicable in fields such as radar and sonar. It will be understood that although the instrumentation, wave properties and frequencies are different in such applications, signal processing and calculation of the cross-correlation function is similar. It is also noted that spatial encoding by mismatched coded waveforms is not limited to a stationary array of elements. The spatial encoding can be implemented in single/multiple-transmitter and single/multiple-receiver system where the element or elements are moving (e.g. according to linear or circular motion).

Use of Mismatched Coded Waveforms for Temporal Encoding

Figure 1B:
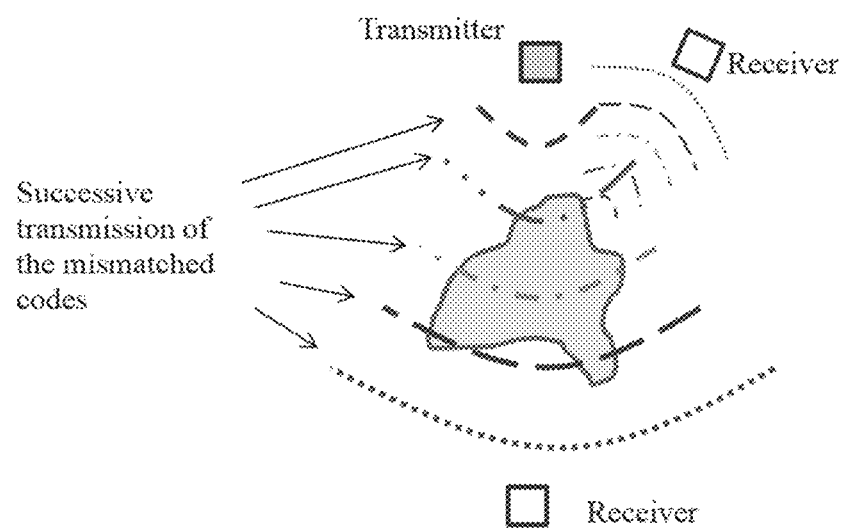

The example coded excitation methods disclosed herein inherently perform temporal encoding that can be used in different application such as ultrasound imaging (Gammelmark, Jensen, IEEE. Trans. Ultrason. Ferroelectr. Freq. Contrl. 22(4), 552-563, 2003). However, the use of mismatched coded waveforms can add the temporal encoding between successively transmitted signals. In other words, employing mismatched transmitted coded waveforms enables the receiver to decode the response to each code, as shown in FIG. 1B, where different mismatched coded waveforms are sequentially transmitted. Such temporal encoding can facilitate high frame rate imaging (signal acquisition) in many applications (e.g. in embodiments in which a plurality of receive elements are employed to facilitate imaging). For example, if one employs a 1 ms transmission from several transducer elements, the example methods disclosed herein may be capable of achieving frame rates of at least 1 kHz.

For example, if a set of receivers are employed (array or several single elements for instance around the target), it will be possible to perform imaging. In a photoacoustic imaging example, the transmitter is a laser light source and receivers are ultrasonic transducers. The laser illuminates the field and target (chromophore) generates the ultrasound that can be detected and converted into image. The use of mismatched coded waveforms in this configuration provides temporal encoding, that is, the receivers don't confuse the signals from subsequent coded waveforms due to their mismatched properties. Therefore, the delay between the subsequent transmissions can be reduced.

Furthermore, if one uses temporally encoded transmissions from one element and an array of receiving elements, similar to the photoacoustic example mentioned above, subsequent low-resolution images can be generated for each code. If a transmitter element can generate diverging beam or plane wave, the receivers will be able to generate one image per code similar to "explososcan" method (Shattuck, et. al J. Acoust. Soc. Am. 1984; 75(4): 1273-1282) or plane-wave compounding (Montaldo, et. al, IEEE Trans. Ultrason: Ferr. Freq. Contr. 2009; 56(3): 489-506).

In conventional pulse transmission methods, it is necessary for the system to interleave sufficient delay time between the successive pulses to ensure that all echoes (responses) associated with the first pulse have been detected, otherwise those remaining signals will be mixed or confused with the responses to the next transmission. Transmitting successive mismatched coded waveforms can reduce this delay time between successive signals without the risk of confusing the responses.

Use of Mismatched Coded Waveforms for Spatial and Temporal Encoding

Figure 1C:
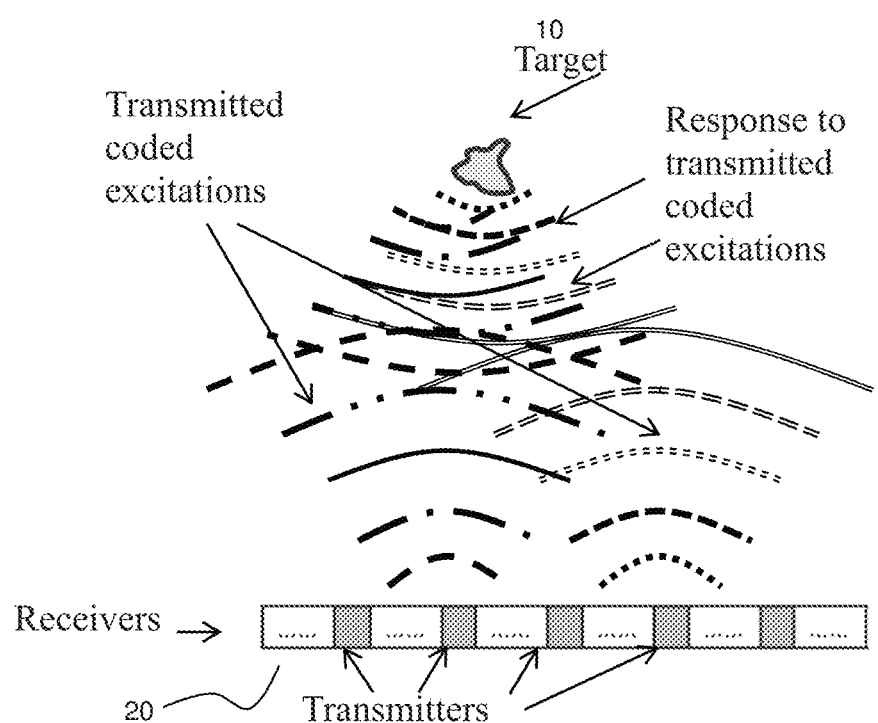

FIG. 1C illustrates a system that is adapted for both spatial and temporal encoding of the excitation energy that is emitted by an array of transducers. By calculating the cross-correlations between the transmitted and detected signal, for each transmitted signal, a set of cross-correlation signals will be generated. The time of transmission and the transmitter (location) are known, thus, the delay time to any returned signal from target can be estimated.

Afterwards, for each time, the low-resolution images can be generated and superposed together. Therefore, several images (the special mapping) of the target for different times can be generated. The collection of images with time can be used to enable high frame rate imaging. Frames obtained using different mismatched coded waveforms are different times can be employed to generate a high-speed time-dependent video (movie) of the target. Accordingly, the example systems and methods provided herein can be useful in facilitating high speed image generation when compared to conventional sequential methods that do not employ mismatched encoding of the imaging energy.

Figure 1D:
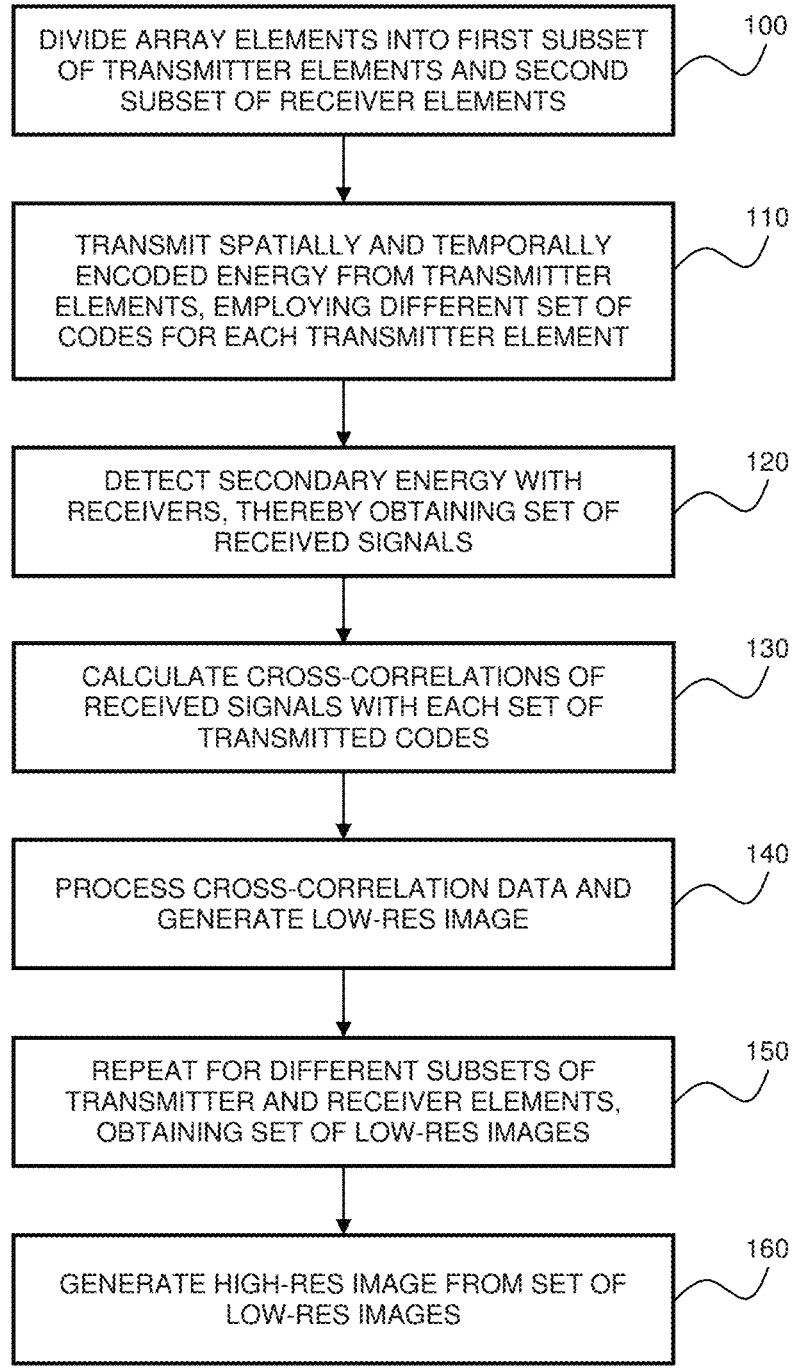
FIG. 1D is a flow chart illustrating an example method of performing imaging involving coded excitation based on both spatial and temporal encoding.

FIG. 1D is a flow chart illustrating an example method of performing imaging involving coded excitation. This example method is based on the configuration shown in FIG. 1C, in which a transducer array is employed, and where at any given time, a first subset of transducers is employed as transmitters, and another subset of transducers is employed as receivers. This division of array elements into transmitters and receivers is shown in step 100. It will be understood that this example method can be readily adapted to other implementations involving different transducer configurations (for example, in the cases of temporal or spatial encoding, as shown in FIGS. 1A and 1B). It will be understood that some or all of the elements can be used, in many application, as transmitters and/or receivers. For example, in one example implementation, after transmitting a code (it should be short enough to finish before receiving back the responses), the transmitter can be switched to act as receiver. In other example implementations, some elements may act as dedicated receivers.

At step 110, the transmitter elements (the subset of elements that are configured as transmitters) are employed to transmit spatially and temporally encoded energy, based on the use of mismatched coded waveforms. Each transmitter element is provided with a separate sequence of mismatched coded waveforms for transmission, such that at any given time, a unique permutation of coded waveforms is employed by the set of transmitters. Secondary energy that is responsively emitted or reflected by the object is detected by the receiver elements (the subset of elements employed as receivers), thereby providing a set of received signals.

The cross-correlation of the set of received signals detected in step 120 with each set of transmitted mismatched coded waveforms is calculated in step 130. In one embodiment, each of these cross-correlations is effectively treated as if one transmission-detection process has been performed at a given point in time. In other words, the cross-correlation calculation effectively extracts response associated with its corresponding code and discards the responses associated with the other coded waveforms.

In step 140, the cross-correlations are processed to generate one or more low-resolution images. The image term "low-resolution" is employed because only a subset of the array elements are employed for transmission and receiving. Known image processing methods (e.g. receive beamforming) are employed to generate the low-resolution image.

Each cross-correlation generates a signal trace that shows the relative distance of the targets. Knowing the speed of wave in the media (for instance sound in the tissue) and also detecting the signal source from cross-correlation, the delay time shows how long it takes for the wave to reach the target and scatter back and detected by the receiver element (the round trip). Therefore, the delay time provides the sum of the distance of the target to transmitting and receiving elements. Thus, knowing the distance of the target to several elements can clarify its position in the space. In some embodiments, the envelope signal may be calculated. The process of image reconstruction can be performed by several methods such as, but not limited to, the algorithm employed in Jensen, J. A., Nikolov, S. I., Gammelmark, K. L., and Pedersen, M. H., Ultrasonics J. 2006; 44:e5-e15. Therefore, any conventional image reconstruction can be employed for low-resolution images, such as beamforming in receive (Szabo, T, Diagnostic Ultrasound Imaging: Inside out, Elsevier, 2004).

In one example implementation, the transmitted code, although transmitted simultaneously with other mismatched coded waveforms, can be treated as single-transmission and one low-resolution image is generated from each. Accordingly, low-resolution image frames can be generated sequentially while processing the image data, yielding a high frame rate of generated images. Alternatively, all of the cross-correlations can be employed to generate a single low-resolution image (having a higher resolution than the low-resolution images described above, but lower resolution than an image that would be obtained using all of the array elements for separate transmission and receiving).

In step 150, steps 100-140 may be repeated one or more times, such that each time these steps are repeated, a different combination of elements is selected as transmitters and receivers. For example, the steps may be repeated such that each element performs both as a transmitter and a receiver at least once. The repeating of the steps generates additional low-resolution images. However, after the complete set of low-resolution images has been obtained, the low-resolution images may be combined to form a high-resolution image, as shown at step 160. The method may then be repeated to provide continuous low and high-resolution imaging. This method thus provides low-resolution images at a high frame rate and high-resolution images at a lower frame rate.

FIG. 1D thus demonstrates an example implementation in which two different subsets of elements of a transducer array are employed for simultaneous imaging. The conventional practice of coded excitation ultrasound imaging consists of transmitting mismatched coded waveforms with durations less than the round trip time for sound to reach focal point and return (O'Donnell M., and, Wang, Y., "Coded Excitation for Synthetic Aperture Ultrasound Imaging," IEEE Trans. Ultrason. Ferroelectr. Freq. Control., 52(2), pp. 171-176, 2005). Therefore, the same set of transducer elements can be switched to perform as receivers.

However, in the present example embodiment (and in the experimental example presented below in FIGS. 14B and 14C), the transmitted mismatched coded waveforms may selected to be long (e.g. 2 ms as in the example shown in FIGS. 14B and 14C)/As a result, as the transmissions were performed from a first subset of transmitter elements, the remaining receiver elements of the array are employed for detecting signals. Afterwards, the cross-correlations of detected signals can be calculated with each code, enabling several low-resolution images to be produced. The number of low-resolution images can be greater than or equal to the number of simultaneously transmitted mismatched coded waveforms. Each low resolution image is generated based on employing a subset of the array elements for transmission and receiving. As noted above, a high resolution image may be generated by superposing the low-resolution images.

Example System for Performing Imaging via Mismatched Code Generation

Figure 2:
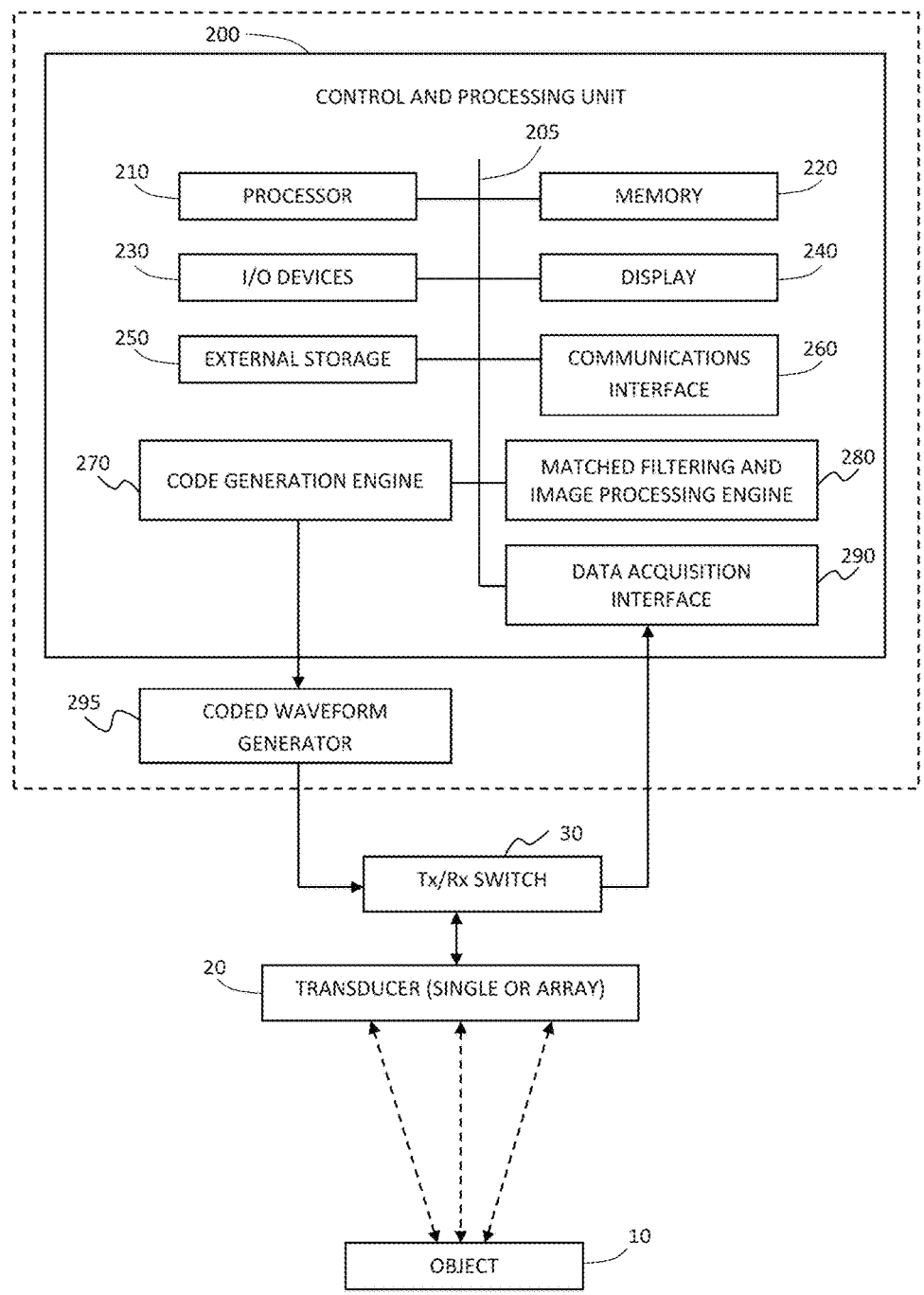
FIG. 2 schematically illustrates an example system for performing various methods of the present disclosure.

Referring now to FIG. 2, an example system is illustrated for performing imaging with mismatched excitation coded waveforms. The system includes a transducer 20 that directs coded excitation energy onto object 10. A control and processing unit 200 is employed to generate the codes (and optionally to generate the mismatched coded waveforms) and to process the detected signals.

As shown in the figure, in the present example system, the coded excitation energy is generated by coded waveform generator 295, and is provided to transducer 20 through Tx/Rx switch 30. Mismatched coded waveform generator 295 receives codes from code generation engine 270 and thereby generates a coded waveform based on a pre-selected waveform type (e.g. sinusoidal). Mismatched coded waveform generator 295 may act as a transducer driver, or may be configured to provide an input to a separate transducer driver (not shown). Energy that is responsively emitted or reflected from the object is detected by transducer 20, and provided, via Tx/Rx switch 30, to a data acquisition interface 290, where the signals are received and subsequently processed by a matched filtering and image processing engine 280 (these are shown as a common engine, but can be implemented as separate engines or modules). It will be understood that an alternative configuration with a second transducer may be employed in a transmission configuration.

As shown in FIG. 2, in one embodiment, code generation engine 270 and matching filtering and image processing engine 280 are implemented as modules within a control and processing unit 200. Control and processing unit 200 may include a processor 210, a memory 220, a system bus 205, one or more input/output devices 230, and a plurality of optional additional devices such as communications interface 260, display 240, and external storage 250.

It is to be understood that the example system shown in the figure is not intended to be limited to the components that may be employed in a given implementation. For example, the system may include one or more additional processors.

One or more components of control and processing unit 200 may be provided as an external component that is interfaced to a processing device. For example, as shown in the figure, mismatched coded waveform generator 295 may be included as a component of control and processing unit 200 (as shown within the dashed line), or may be provided as one or more external devices.

Embodiments of the disclosure can be implemented via processor 210 and/or memory 220. For example, the functionalities described below can be partially implemented via hardware logic in processor 210 and partially using the instructions stored in memory 220. Some embodiments are implemented using processor 210 without additional instructions stored in memory 220. Some embodiments are implemented using the instructions stored in memory 220 for execution by one or more general purpose microprocessors. Thus, the disclosure is not limited to a specific configuration of hardware and/or software.

As shown in the figure, control and processing unit 200 includes code generation engine 270 and matched filtering and image processing engine 280, which comprises algorithms for performing the methods described herein, stored as computer-readable instructions in memory 220 to be executed by processor 210.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

Mismatched Code Generation Employing Multiple Dissimilar Chirps per Code

Figure 3A:
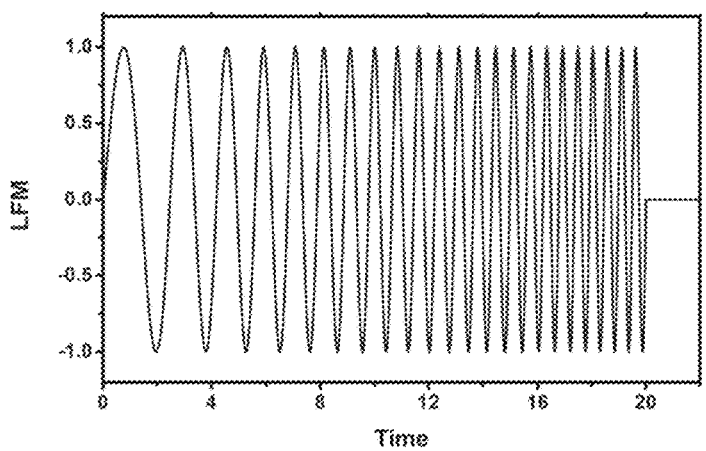
FIGS. 3A-C shows (A) a linear frequency modulation chirp, (B) the envelope cross-correlation (cross-correlation) function of the chirp, and (C) frequency sweep of the chirp versus time.
Figure 3B:
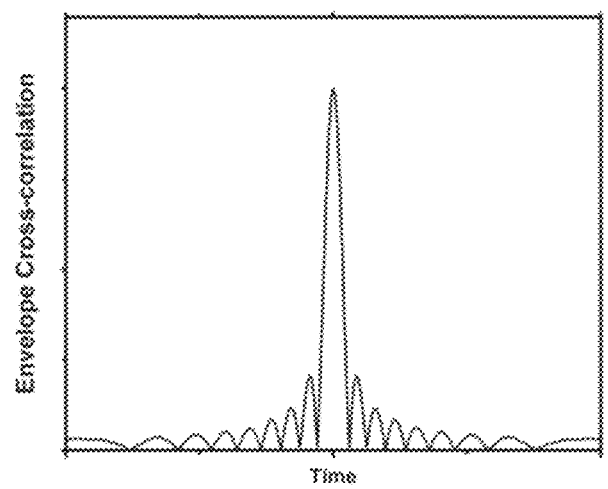
Figure 3C:
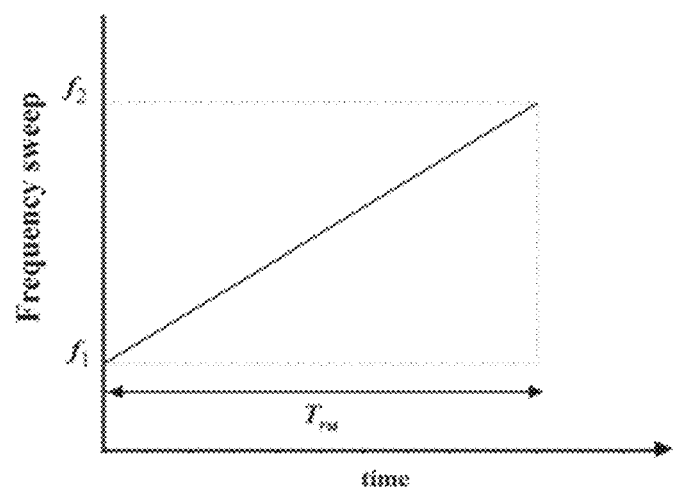

The present example embodiment involves the use multiple chirps (frequency modulations) per code for the generation of mismatched frequency-modulated codes. A typical example of a frequency modulation signal is a linear frequency modulation (LFM) with sinusoidal carrier which can be defined as:

$$r(t) = A\sin\left(2\pi f_1 t + \frac{\pi(f_2 - f_1)}{T_{FM}}t^2\right) \quad (1)$$

$$0 < t < T_{ch}, \text{ and, } B_{ch} = |f_2 - f_1|$$

where t is time, A is the amplitude, $T_{ch}$ is the chirp duration, $B_{ch}$ is the frequency bandwidth of the chirp and $f_1$ and $f_1$ are the starting and ending frequencies, respectively. FIGS. 3A-C show a typical linear frequency modulation, its envelope cross-correlation (cross-correlation) function and its frequency sweep during time $T_{FM}$, respectively. The cross-correlation function can be computed using the inverse Fourier transform as shown in Eq. (2):

$$B(t) = \frac{1}{2\pi} \int_{-\infty}^{+\infty} r^*(\omega) r(\omega) e^{i\omega t} d\omega \qquad (2)$$

Figure 4:
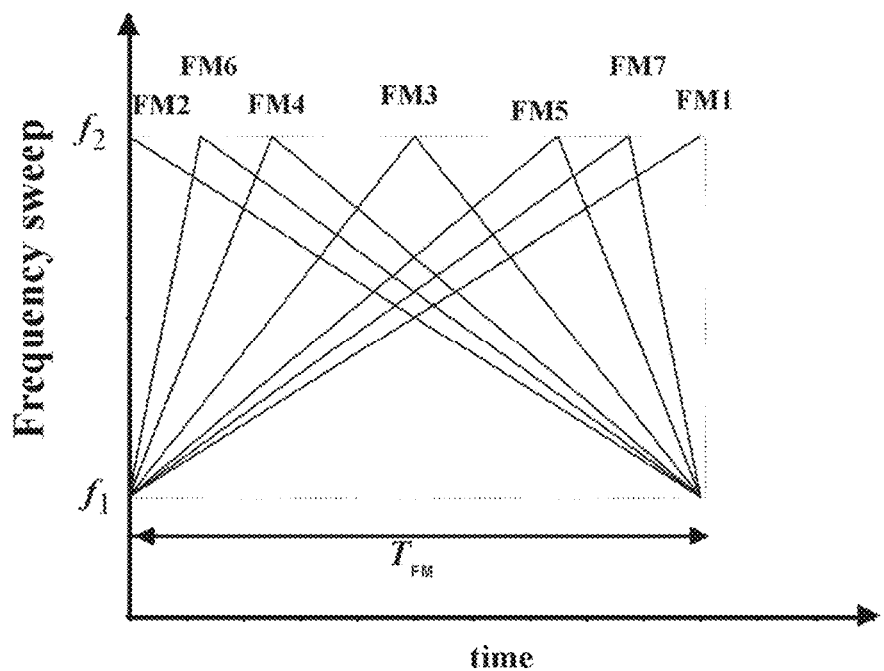
FIG. 4 illustrates frequency sweeps with identical bandwidth and center frequency (CF), generating mismatched frequency modulations (FM). FM1 and FM2 are up-chirp and down-chirp. FM4 to FM7 are examples of the embodiments involving mismatched frequency modulated code generation, employing multiple chirps per code with dissimilar slopes.

FIG. 4 shows time-dependent profiles of several example frequency sweeps for generating mismatched FM signals. FM1 and FM2 are single-sweep chirps (increasing and decreasing) that are known in the ultrasound art. The frequency of the chirp may increase or decrease with time, (for example, see FM1 and FM2 in FIG. 4, which show increasing and decreasing chirps, respectively). Also, the carrier waveform is not required to be sinusoidal, but can employ other waveform types, such as, but not limited to, square, triangle, and, ramp.

According to the present example embodiment, multiple mismatched coded waveforms are generated by dividing the time duration of each frequency-modulated (FM) coded waveform into two or more time divisions, where each time division is chirped at a different slope, and where at least two of the different chirps associated with the different time divisions overlap in bandwidth, at least in part, and where the various mismatched coded waveforms overlap in bandwidth, at least in part. The slope of a given mismatched coded waveform, within a given time division, is different from slopes of the same coded waveform in other time divisions of the same coded waveform, as well as different from the slopes of the other coded waveforms at any of their respective time divisions. As such, a given slope can only be used once in a set of mismatched coded waveforms—within any of their time divisions. In other words, the mismatched coded waveforms are generated such that the slopes of sweeps in different coded waveforms, as well as different divisions of the coded waveforms, are dissimilar, that is, each slope has been used only once in a set of mismatched frequency modulation coded waveforms.

As noted above, according to one example embodiment, the frequency ranges of at least two different sweeps (sub-chirps) in within each code are at least partially overlapping, and the frequency ranges of each code are overlapping, at least in part. For example, the degree of overlap between the frequency ranges of any two time divisions within a mismatched coded waveform, or within any two coded waveforms as a whole, may be greater than 10%, greater than 25%, greater than 50%, greater than 60%, greater than 70%, greater than 80%, greater than 90%, or greater than 95%. In one example implementation, the frequency ranges of all of the different sweeps, within a given code, and/or within all coded waveforms, are equal. In another example implementation, the frequency ranges of all of the different sweeps within a given code, and/or within all coded waveforms, are overlapping. In another example implementation, the frequency ranges a first subset of sweeps of a given code or a first subset of coded waveforms are overlapping, while the frequency ranges of another subset of sweeps of the given code or another subset of coded waveforms are overlapping, respectively.

In one example implementation, the mismatched coded waveforms are selected such that at least a subset of the coded waveforms has identical code lengths (durations). In another example implementation, the mismatched coded waveforms are selected such that all of the codes have identical code lengths (durations).

Some example embodiments presented here may be useful for generating a wide number (unlimited in theory) of mismatched coded excitations. In some embodiments, mismatched coded waveforms are generated with the same frequency and duration (length). In the frequency modulation cases described herein, linear frequency sweeps can be employed to generate identical signal-to-noise ratio and resolution for all simultaneously transmitting signals, which is useful in many applications, such as biomedical ultrasound. However, the methods are not restricted or limited by the abovementioned properties.

Since a linear frequency modulation generates the maximum SNR (signal-to noise ratio) (Misaridis, T. and, Jensen J. A. 2005) and is the most commonly used frequency modulation type, the examples employed here use this kind of frequency sweep. If linear frequency sweeps are employed in time divisions, it will not enforce any weighting on the frequency ranges, and all frequencies will be employed uniformly. However, it will be understood that the examples involving linear sweeps are provided merely for illustrative purposes, and that in other embodiments, the slope may be non-linear.

In some embodiments, mismatched coded waveforms are generated with identical length and bandwidth, therefore they produce uniform SNR and resolution for all transmissions. However, this should not be considered as the constraint or limitation, and that in other implementations, coded waveforms with different lengths, and/or bandwidths, may be employed.

Referring now to FIG. 4, FM3 to FM7 illustrate example frequency modulations (FMs; i.e. frequency sweeps; chirps) that are generated according to the aforementioned criteria involving multiple chirped time divisions with dissimilar slopes. It can be seen that the slope within each time division of the FMs is different from that of time divisions of the same FM, as well as each part of the other FMs.

As noted above, in one example embodiment, at least two of the frequency sweeps in time divisions of the mismatched coded waveforms (or frequency ranges of different coded waveforms in the set of mismatched coded waveforms) have total or partial overlap. The degree of mismatch between the coded waveforms is related to the difference between the slopes within the various time divisions of each code, where larger differences generally produce improved results. Accordingly, it has been found that slopes with the same magnitude yet with opposite signs generate the minimum cross-correlation between the FM coded waveforms.

The example mismatched coded waveforms shown in FIG. 4 consist of linear sweeps and share the same bandwidth as well as duration (length). These properties have been found to be advantageous, but they are not the necessary conditions for application of the present example method.

For example, in one example embodiment, the frequency range of the FM may be selected to be equal for all coded waveforms, as illustrated in the example FM profiles shown in FIG. 4. As shown in FIG. 4, the slope changes over the full frequency range within the time interval of each sub-chirp. Therefore, the aforementioned condition that the slope is distinct for each time division is equivalent to choosing distinctive time intervals for intra-code and inter-code chirps (if the same frequency range employed for all sub-chirps); with the additional consideration that for each code, two mismatched chirps are employed with positive and negative slopes. FM3 is an example demonstrating this property, where the time divisions have the same interval ($T_{FM}/2$), and therefore they have opposite slopes. Similarly, for example, the parts in FM4 and FM5 with identical intervals can be exchanged, that is, using the same intervals and replacing increasing-decreasing and decreasing-increasing chirps with increasing-increasing and decreasing-decreasing chirps. However, this change will not add any additional FM to the mismatched set.

Figure 5:
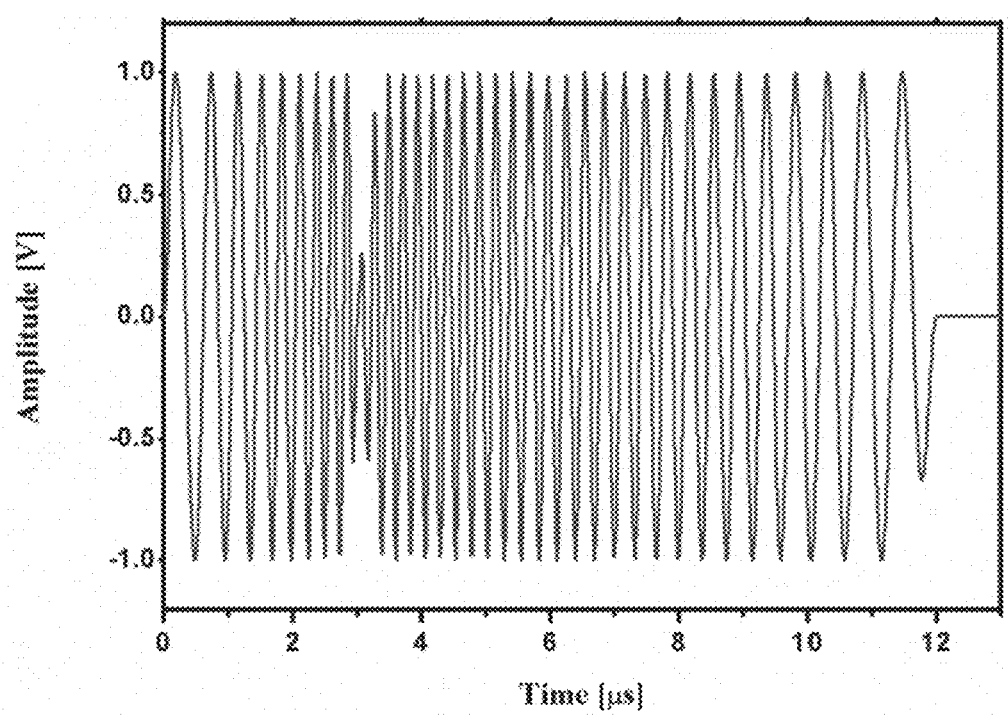
FIG. 5 plots an example of a waveform based on the method of mismatched frequency modulated code generation (FM4 in FIG. 3), showing a new chirp by dividing the bandwidth into two parts and sweeping with different slopes.

FIG. 5 shows an, example waveform corresponding to the FM4 chirp of FIG. 4. The example FM signals shown in FIG. 4 have one increasing portion and one decreasing portion, illustrating one example implementation of the present embodiment. In the first part the frequency increases from $f_1$ to $f_2$ in $0.25 \times T_{FM}$ and then the frequency decreased from $f_2$ to $f_1$ in $0.75 \times T_{FM}$. The duration of the chirp is arbitrary and can be specified by the slope of the frequency sweep. Therefore, dividing the chirp duration into two or more parts is readily achievable. However, the duration of any of the frequency sweeps should be large enough to allocate several cycles of middle frequencies as well. Here we can add that one advantage of the proposed method is that it is easy to generate a computer algorithm to automatically produce the required number of mismatched coded waveforms. The slopes can be chosen to be positive or negative, as long as the aforementioned condition involving the slopes is satisfied; namely that the slopes are different in different time divisions of each code (e.g. FM9 in FIG. 6). In other words, the inter-code and intra-code slopes should be different, where the intra-code requirement stipulates that slopes are different among different time divisions within a code, and the inter-code requirement stipulates that slopes are different among any parts of the two mismatched coded waveforms.

Figure 6A:
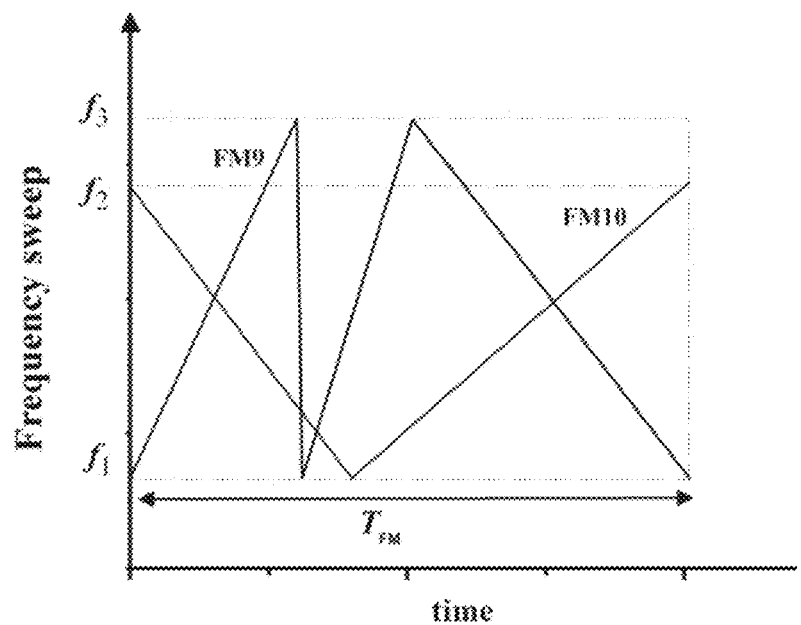
FIG. 6A plots two additional examples of the example embodiment involving mismatched frequency modulated code generation employing multiple chirps per code with dissimilar slopes, where FM9 is generated by dividing the bandwidth into three sections and sweeping with three different slopes, and FM10 is generated by sweeping the bandwidth partially.
Figure 6B:
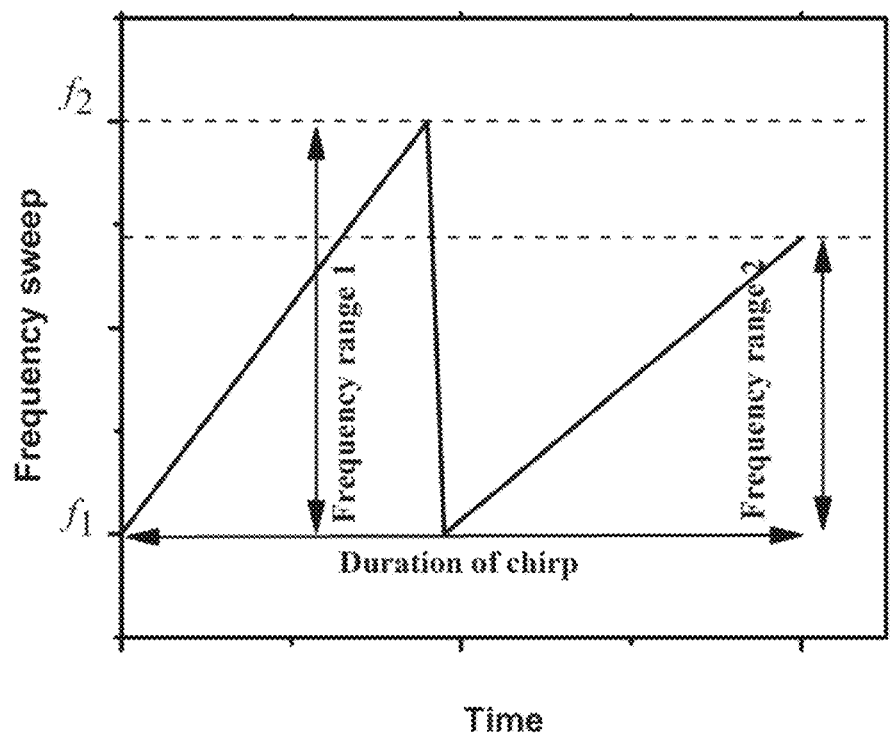
FIG. 6B plots an example of a code in which different time divisions employ different yet overlapping frequency ranges.

FIGS. 6A and 6B illustrates additional example waveforms. FIG. 6A plots two additional examples of the example embodiment involving mismatched frequency modulated code generation employing multiple chirps per code with dissimilar slopes, where FM9 is generated by dividing the bandwidth into three sections and sweeping with three different slopes, and FM10 is generated by sweeping the bandwidth partially. FIG. 6B plots an additional example of the example embodiment involving mismatched frequency modulated code generation employing multiple chirps per code with dissimilar slopes, where FM11 is generated by dividing the bandwidth into two sections and sweeping the overlapping bandwidth with two different slopes. Both slopes of this example are positive.

It is noted that the present embodiment is not limited to two time divisions, and can be implemented with three or more divisions. An example of a frequency sweep with three time divisions is shown in FM9 in FIG. 6A. As noted above, the slope within each time division should not be repeated within a given code (i.e. distinct intra-code chirps) and should not be repeated among other mismatched coded waveforms (i.e. distinct inter-codes chirps). Also, as noted above, the general performance of the coded waveforms in producing mismatched signals will be improved for slopes that have increased differences in slopes.

It is also noted that that it is not required that all of mismatched coded waveforms in a mismatched set share the same bandwidth. However, in one example implementation of the present method, completely or partially shared bandwidth (within a given coded waveform, or among different coded waveforms) may be employed. For instance, in phased array ultrasound imaging, it may be preferable to use a higher range of frequencies in the middle portion of the array and a lower frequency range in the sides of the array during the transmission. In one implementation, bandwidths with shared portions are employed while using mismatched coded waveforms (e.g. FM10 and FM9 in FIG. 6). It should be added that if dissimilar frequency ranges are employed, then the duration divisions do not necessarily need to be different to generate dissimilar slopes.

Although the examples presented herein employ sinusoidal carrier waves for chirps, it will be understood that methods disclosed herein can be readily implemented with other waveforms, such as, but not limited to, square, triangle, ramp, and other waveforms.

Figure 7:
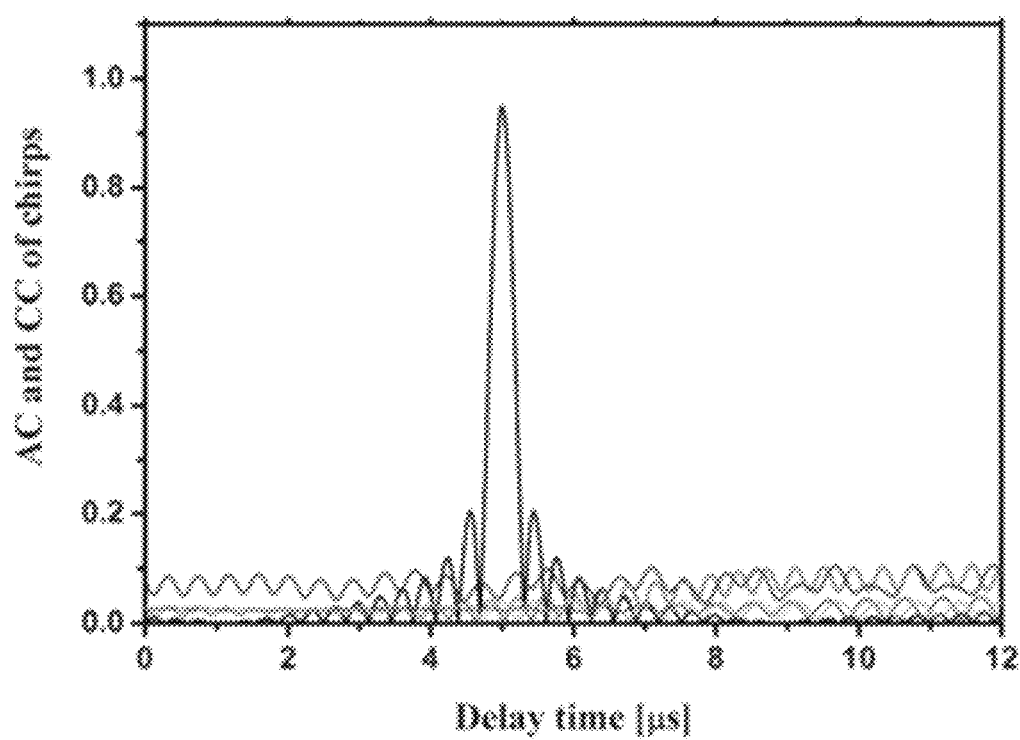
FIG. 7 plots the auto-correlation of FM4 and cross-correlation of FM4 with four other FM chirps, providing an example of autocorrelation and cross-correlation of mismatched codes generated by the example embodiment involving mismatched frequency modulated code generation employing multiple chirps per code with dissimilar slopes.

FIG. 7 shows the autocorrelation of one of the coded waveforms (FM4) in FIG. 4 and its cross-correlation with other frequency modulation coded waveforms (i.e. FM1, FM2, FM3, and FM7). The envelope autocorrelation of FM4 is similar to any other code in FIG. 7; they have the same peak value, resolution (full-width at half-maximum) and similar sidelobes. On the other hand, the cross-correlation of any of these coded waveforms with others will have some variations. The cross-correlation between the mismatched coded waveforms can be reduced by increasing the duration of the signal and/or increasing the frequency range. However, in practice, these parameters can be limited by constraints imposed by the hardware employed. Additional techniques can also be employed to reduce the cross-correlations between the coded waveforms, however these techniques require multiple transmission-detection and averaging.

Mismatched Code Generation Employing Concatenated Multi-Frequency Binary Phase-Coded Waveforms The present example embodiment involves the use of binary phase-coded waveforms for the generation of mismatched multi-frequency coded waveforms. One non-limiting example of a binary code is a Golay Code. A Golay Code is a complementary bipolar sequence defined as a pair of N-bit length binary sequences, A(k) (k=0, 1, . . . , N−1) and B(k) which satisfies:

$$A(k)*A(-k)+B(k)*B(-k)=2N\delta(k), \quad (3)$$

where * represents convolution and δ(k) represents the Dirac delta function and A(−k) and B(−k) represents the code with the reverse order. In other words, a Golay code consists of two N-bit sequences where the sum of autocorrelations of these two codes is zero everywhere except at zero time where it is equal to 2N. (Golay, IRE Trans. Inf. Theory IT-7:82-87, 1961).

As noted above, a Golay Code has two complementary parts, A(k) and B(k), which are each convolved with a waveform (such as a sinusoid or other waveform). Both parts of a Golay code (e.g. the A(k) and B(k) here) always have the same length. As it is clear from the definition of the Golay code, the cross-correlation of response to each part of the code should be calculated with its corresponding transmitted code, and then, the two cross-correlations are added.

In some embodiments, the two parts of the Golay coded waveform are transmitted separately in time, such that the responses are collected separately in time. Because the coded waveform have a non-zero cross-correlation, any overlap in receiving the two complementary coded waveforms generate unwanted cross-correlation. However, it will be understood that in alternative embodiments, simultaneous transmission of Golay code complementary parts can be performed, provided that multiple transmission and Hadamard decoding are used to separate the mixed cross-correlations (e.g. as described in Chiao and Thomas, U.S. Pat. No. 6,048,315).

After generation of the coded excitation signals and directing the coded excitation energy onto the object being imaged, the measured signal that is responsively detected is match-filtered to within each Golay Code and its complement. The two matched filtered signals for each Golay Code are added to cancel the sidelobes. In a step by step method, first the one part of the Golay code is transmitted (e.g. A(k)) and the response is detected. Afterwards, the complementary code is transmitted (e.g. B(k)) and its response is detected. The cross-correlation of each part with its corresponding code is calculated and then the two cross-correlations are added to cancel the sidelobes. This addition shows the location of the target (similar to FIG. 8C).

When employed for encoding signals, the signal enhancement of a Golay Code is proportional to 2N, the length of the Golay Code, regardless of carrier waveform. For example, Equation (3) shows that the signal enhancement is proportional to the length of the sequence and ideally no sidelobes are present. It will be understood that many different carrier waveforms can be employed for the transmission of a Golay Code. The use of half-cycle sinusoids generates Golay coded waveforms with cross-correlation sums that have no sidelobes, similar to the binary Golay codes.

Several matched Golay coded waveforms can be generated by concatenating individual Golay Codes with waveforms having different carrier frequencies.

Figure 8A:
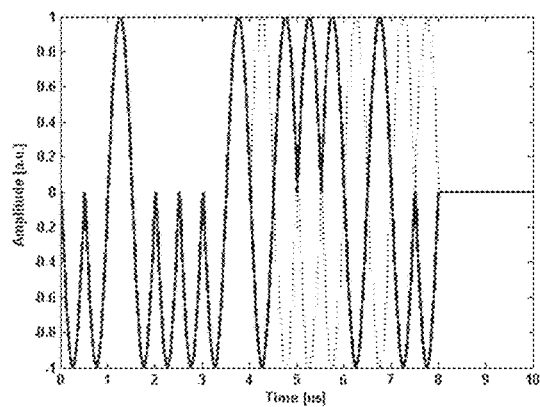
FIG. 8A-C plots (A) a half-cycle sinusoidal 16-bit Golay code, (B) a 8-bit full-cycle sinusoidal Golay Code; the A(k) part of the Golay Codes are shown in solid lines and the complementary parts (B(k) in Eq. (3)) are shown in dotted lines; and (C) the addition of complementary auto-correlations for both cases, (A) and (B).
Figure 8B:
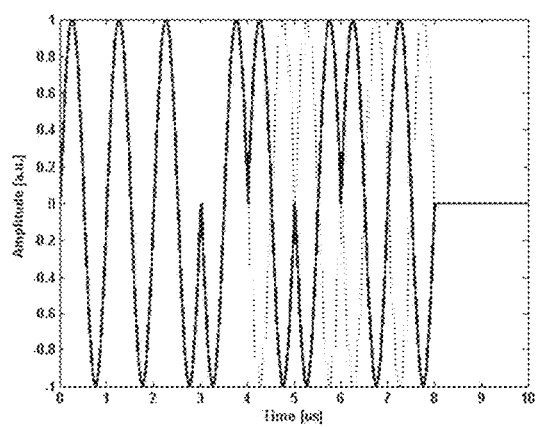
Figure 8C:
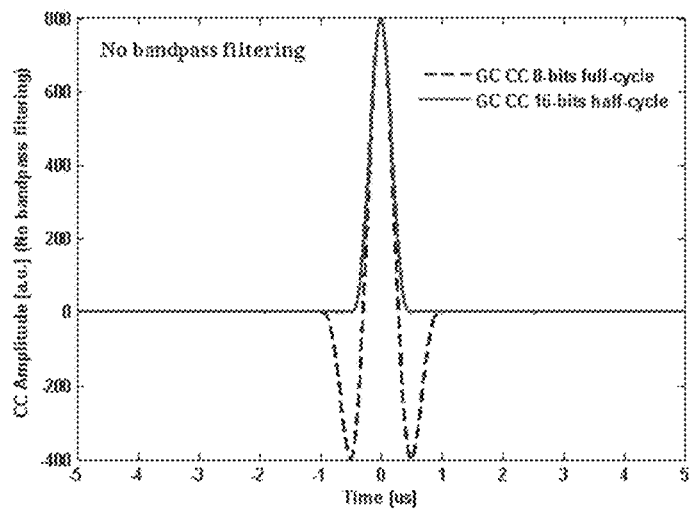

FIGS. 8A-C show (A) a half-cycle sinusoidal 16-bit Golay Code, (B) an 8-bit full-cycle sinusoidal Golay Code, and (C) the addition of the complementary auto-correlation (Eq. 3) for both cases. In FIGS. 8A and 8B, the A(k) part of the Golay Codes are shown in solid lines and the complementary parts (B(k) in Eq. 3) are shown in dotted lines.

In the present example embodiment, mismatched Golay coded waveforms are generated based on the use of concatenated waveforms with different frequencies:

In one example implementation, a set of mismatched Golay coded waveforms with identical length can be generated with the following steps:

Step 1: The length of the original Golay code (number of bits, $N_b$), the center frequency ($f_c$) and the carrier waveform, and the half-cycle (HC) or full-cycle (FC) type of waveform are specified. The sampling frequency ($f_s$) is also specified.

Step 2: A cycle of carrier waveform (HC or FC based on the selection in step 1) with the center frequency ($f_c$) is generated. The length of this cycle is $N_{1c}=\text{Int}(fs/fc)$ or round(0.5*fs/fc) for FC and HC, respectively. Here Int( ) is a function that returns the nearest integer by rounding the value.

Figure 9:
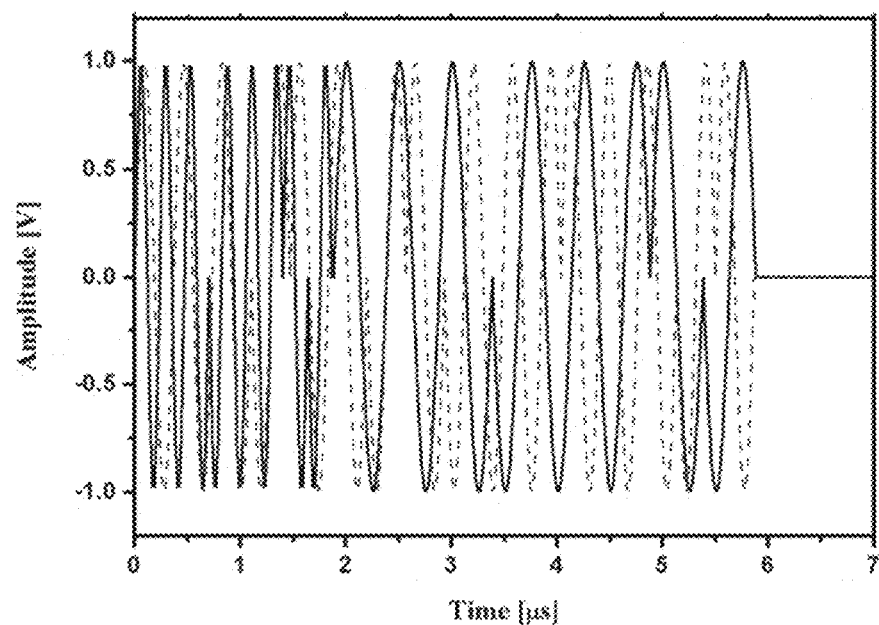
FIG. 9 plots a conventional 16-bit Golay Code (dashed line) with sinusoidal carrier and a compound Golay Code (solid line) generated by concatenating two 8-bit Golay Codes with different frequencies. The complementary codes will be generated similarly.

Step 3: In a loop, from 1 to $N_b$, the two complementary parts of a conventional Golay code are generated. The template cycle generated in step 2 is multiplied by values of bits of Golay code A(k) (and separately by B(k)) and concatenated in the order of bits. For example the 16-bit Golay code in FIG. 9 shown with dashed lines is generated based on FC, sinusoidal, and center frequency of 2.72 MHz and using sampling frequency of 30 MHz, the length of each cycle is 11 points.

Step 4: In the present non-limiting example implementation, the other Golay codes are generated by concatenating two Golay codes with half the length of the original Golay code; that is $N_b/2$. Usually, Golay codes are generated with length $N_b=2^N$, therefore, a Golay code with length $N_b/2$ should be readily available. The carrier wave cycle template for each code should be generated. The length of the template cycle for the two sub-Golay codes can be chosen according to $N_{1c}\pm n$, that is with adding and subtracting an integer value from number of points in the Golay code carrier cycle in step 2, the length of the carrier wave for the concatenating cycles are identified. Thus, the two new carrier wave templates can be generated. For example in the case described above, we can have next templates with lengths 10 and 12 per cycle (n=1). With sampling frequency of 30 MHz, these values correspond to center frequencies of 3 and 2.5 MHz, respectively. Choosing an 8-bit length Golay code for this case, the length of concatenated Golay code is exactly similar to the previous case. Thus, specifying the lengths, two template carrier wave cycles are generated.

Step 5: Similar to step 3, two Golay codes with length $N_b/2$ are generated and concatenated together. The complementary concatenated Golay codes are also generated similarly.

Step 6: Steps 4 and 5 are repeated for another values of n, for instance n=2, 3, . . . and new set of concatenating Golay codes with the same length of the original is produced. In FIG. 9, the solid lines show a concatenated Golay code (each part 8-bits) generated with temple cycles of 7 and 15 points (n=4), corresponding to 4.286 and 2 MHz respectively.

This algorithm can be modified, if one needs to generate new Golay codes with concatenating three or more Golay codes together. It is readily applicable for case of four Golay codes as Golay codes with length $N_b/4$ is most probably available, but for other numbers such as three or five, one needs to search for available lengths of Golay code and may require to compromise in the length or average frequency of the waveform. Also, the above mentioned algorithm is based on using a template cycle and generating the Golay code waveform based on that, however, it is not the constraint of the method. One may specify the sampling rate and center frequency of a Golay code and generate each part of one Golay code, then concatenate the Golay codes, such that the cycles in one code are not identical (not generated from one template) but generated based on sampling frequency. It should be emphasized that the main condition here is that each frequency in the set of mismatched codes should only be used once. That is, if one frequency is used in one of the sub-Golay codes, it should not be used in another sub-Golay code of the same or other concatenated or the original not-concatenated Golay code (It should be clarified that the same frequency should however, be used in the sub-Golay of complementary part of the same code.)

Figure 8D:
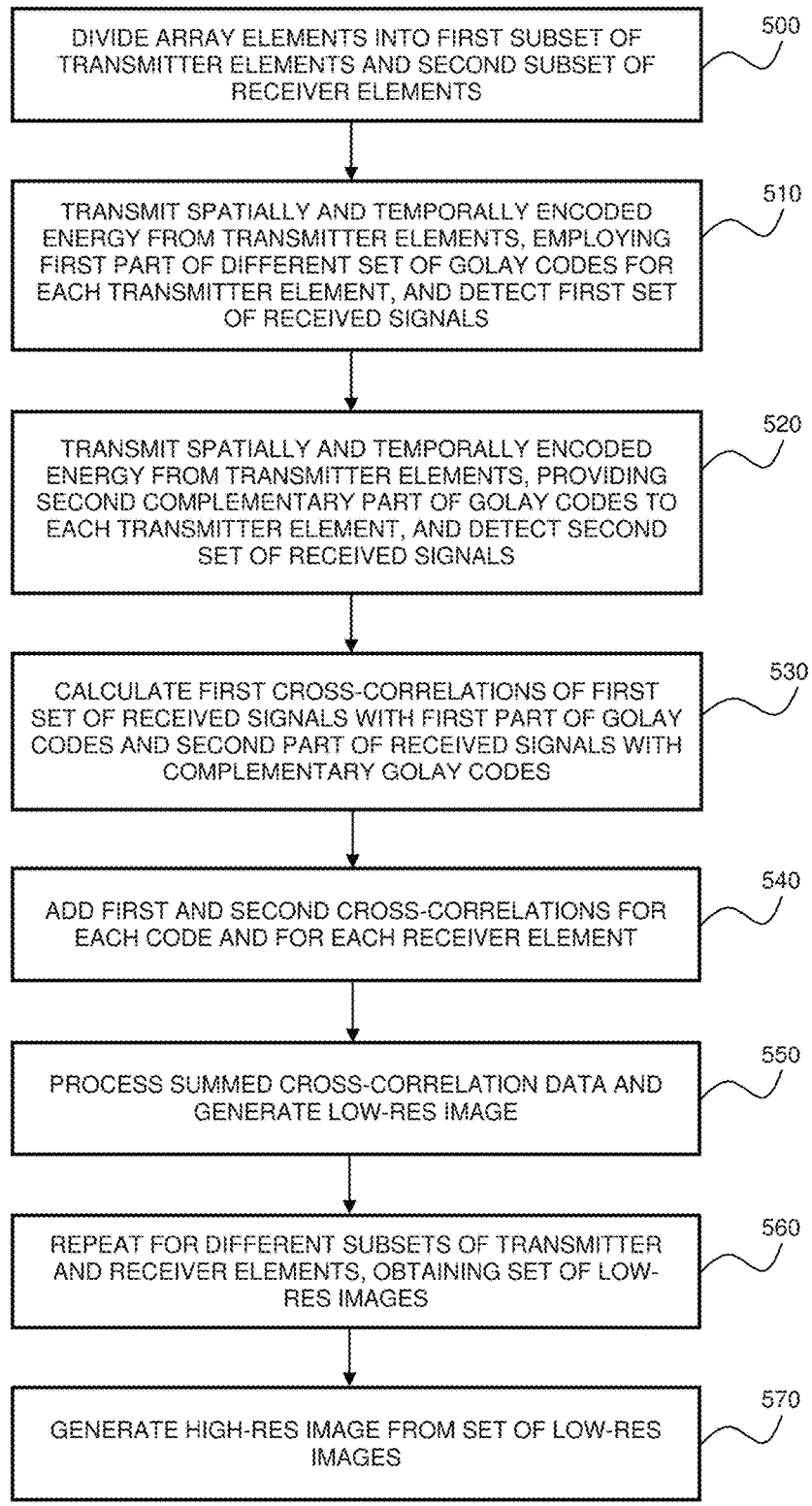
FIG. 8D is a flow chart illustrating an example method of performing imaging involving coded excitation based on concatenated multi-frequency Golay Codes.

As described above in FIGS. 1A-D, coded imaging can be performed in a number of different configurations, where FIG. 1D illustrated the case of coded imaging with spatial and temporal encoding using a transducer array. FIG. 8D is a flow chart illustrating an example method of performing imaging involving coded excitation based on concatenated multi-frequency Golay coded waveforms. The reference mismatched Golay code sets can be stored and used from memory, and may be generated as described above.

This example method is based on the configuration shown in FIG. 1C, in which a transducer array is employed, and where at any given time, a first subset of transducers is employed as transmitters, and another subset of transducers is employed as receivers. This division of array elements into transmitters and receivers is shown in step 100. It will be understood that this example method can be readily adapted to other implementations involving different transducer configurations (for example, in the cases of temporal or spatial encoding, as shown in FIGS. 1A and 1B).

At step 510, the first parts of all Golay coded mismatched waveforms are transmitted by the transmitter elements and the response is detected by the detector elements, and the secondary energy that is responsively emitted or reflected by the object being imaged is detected by the receiver elements as a first set of received signals. Subsequently, in step 520, the complementary parts of the same set of mismatched Golay coded mismatched waveforms are transmitted and a second set of signals are detected by the receiver elements.

The cross-correlation of the first set of signals is calculated in step 530, where the cross-correlation is calculated based on the first part of all transmitted Golay coded mismatched waveforms. Each of these cross-correlations is treated as if one transmission-detection process has been performed. In other words, the cross-correlation calculation effectively extracts response associated with its corresponding Golay code and discards the responses associated with the other mismatched coded waveforms. Similarly, in step 540, the cross-correlation of the second set of signals is calculated, where the cross-correlation is calculated based on the second (complementary) part of all transmitted Golay coded mismatched waveforms.

As shown in step 540, the two parts of each calculated cross-correlation, for each Golay code, and for each detection element, are added together. This generates a signal trace that shows the relative distance of the targets. Knowing the speed of the probe wave in the media (for instance sound in the tissue) and also detecting the signal source from cross-correlation, the delay time shows how long it takes for the wave to reach the target and scatter back and detected by the receiver element (the round trip). Therefore, the delay time provides the sum of the distance of the target to transmitting and detecting elements. Thus, knowing the distance of the target to several elements can clarify its position in space. In some embodiments, the envelope signal may be calculated.

In step 550, the cross-correlations are processed to generate one or more low-resolution images. The term "low-resolution" is employed because only a subset of the array elements is employed for transmission and receiving. Known image processing methods (e.g. receive beamforming) are employed to generate the low-resolution image.

Time-of-flight information can be obtained by processing the cross-correlation data. Images can be reconstructed. In this step, signals from each transmitted Golay code and detected by all receivers are used together. That means each transmitted Golay code, although transmitted simultaneously with other mismatched coded waveforms can be treated as single-transmission and one low-resolution image is generated from each. The process of image reconstruction can be performed by several methods, such as, but not limited to, the algorithm employed in Jensen, J. A., Nikolov, S. I., Gammelmark, K. L., and Pedersen, M. H., Ultrasonics J. 2006; 44:e5-e15. As mentioned, in this step, the signals generated by pulse compression with each transmitted code are treated together and separate from signals due to pulse compression with other transmitted coded waveforms. Therefore, any conventional image reconstruction can be employed for low-resolution images, such as beamforming in receive (Szabo, T, Diagnostic Ultrasound Imaging: Inside out, Elsevier, 2004).

In step 560, steps 500-550 may be repeated one or more times, such that each time these steps are repeated, a different combination of elements are selected as transmitters and receivers. For example, the steps may be repeated such that each element performs both as a transmitter and a receiver at least once. The repeating of the steps generates additional low-resolution images. However, after the complete set of low-resolution images has been obtained, the low-resolution images may be combined to form a high-resolution image, as shown at step 570. The method may then be repeated to provide continuous low and high-resolution imaging. This method thus provides low-resolution images at a high frame rate and high-resolution images at a lower frame rate.

Referring now to FIG. 9, an example of such a concatenated multi-frequency Golay Code is illustrated. This figure shows a 16-bit code (dashed line) and two concatenated 8-bit mismatched coded waveforms (solid lines). The frequencies of the two 8-bit coded waveforms are chosen in a way that they yield approximately an averaged frequency of the original 16-bit code. The two complementary Golay Codes (that are complements of the two 8-bit codes) are also produced similarly: using the same frequencies as in the initial two 8-bit codes, and concatenating the waveforms.

Although the example that is shown in FIG. 9 illustrates the generation of complementary concatenated Golay coded mismatched waveforms based on a set of two concatenated coded waveforms, it will be understood that the present example embodiment is not limited to the concatenation of two coded waveforms, and that generally, two or more coded waveforms can be concatenated.

Figure 10:
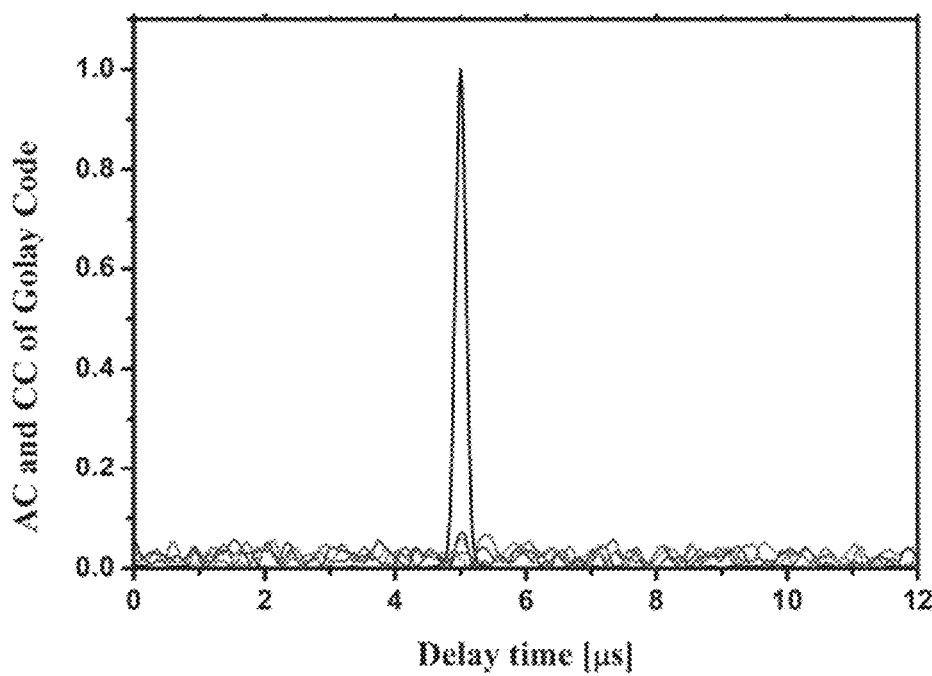
FIG. 10 plots an example of autocorrelation and cross-correlation of mismatched codes generated by an example method involving mismatched code generation employing concatenated multi-frequency Golay Codes, showing the autocorrelation of a concatenated Golay Code and its cross-correlation with four other codes. All Golay Codes share the same length and approximately identical center frequency.

FIG. 10 plots the addition of complementary autocorrelations of one of these coded waveforms. This Golay coded mismatched waveform is generated by concatenating two full-cycle 256-bit Golay codes with center frequencies 2 and 4.28 MHz. This figure also shows the cross-correlation of selected Golay Code with other mismatched codes, where all of mismatched coded waveforms have identical length. Three of the Golay coded waveforms are generated by concatenating two 256-bit Golay codes with center frequencies in each set 2.5 and 3 MHz, 2.3 and 3.3 MHz, 2.14 and 3.75 MHz. Also there is a 512-bit Golay coded waveform with center frequency of 2.72 MHz. The envelope signal shows the typical shape of the Golay coded waveform cross-correlation with no sidelobe extension on the sides of the main lobe. The cross-correlations with other coded waveforms are very small compared with the main peak. It should be added that the cross-correlation of each part of the complementary coded waveforms with other coded waveforms is calculated separately (the A(k) part with A(k) part for all, and B(k) part with B(k)) and the resulting cross-correlations are added together similar to the real simultaneous application of the mismatched coded waveforms.

The method of concatenating mismatched coded waveforms with different frequencies to generate long mismatched coded waveforms is compatible with other types of phase-coded waveforms such as binary phase-coded waveforms. Among the widely used binary phase-codes are Barker codes, however, their available lengths are very limited (Barker codes with maximum length of 13 bits are available). In other example implementations, other types of mismatched codes may be employed, such as, but not limited to, Frank codes, Zadoff-chu codes (Nadav, L., and Mozeson, E., Radar Signals, Wiley, 2004), and m-sequences, and Gold-sequences.

Mismatched Code Generation Employing Chirped Binary Phase-Coded Waveforms

The present example embodiment involves the use of binary phase-coded waveforms for the generation of mismatched multi-frequency coded waveforms. Although Golay codes are used as examples of binary codes, it will be understood that many different types of binary phase codes having low cross-correlation may be employed, such as those described in the previous section.

As noted above, the commonly used carrier waveforms for Golay Code based transmission are either half-cycle or full-cycle, sinusoidal or square waves. In contrast, according to the present example embodiment, a chirped carrier (i.e. a frequency-modulated carrier) is employed for the transmission of Golay coded waveforms, such that each bit of the phase-coded waveform is chirped. In other words, a chirped waveform can be coded to generate a new form of coded excitation. The pulse compression signal of such a coded excitation can be calculated in a manner very similar to a conventional Golay Code.

According to the present example embodiment, the degree of overlap between the frequency ranges within any two coded waveforms, may be greater than 10%, greater than 25%, greater than 50%, greater than 60%, greater than 70%, greater than 80%, greater than 90%, or greater than 95%. In one example implementation, the frequency ranges within all coded waveforms are equal. In another example implementation, the frequency ranges within all coded waveforms are overlapping. In another example implementation, the frequency ranges of a first subset of coded waveforms are overlapping, while the frequency ranges of another subset of coded waveforms are overlapping.

In one example implementation, the mismatched coded waveforms are selected such that at least a subset of the coded waveforms has identical code lengths (durations). In another example implementation, the mismatched coded waveforms are selected such that all of the codes have identical code lengths (durations).

According to the present example implementation, pulse compression of each code part is calculated with its corresponding code and the two matched filter signals are added to yield the final pulse compression signal. Here it should be added that the employed chirp itself can have a sinusoidal, square, or other type of carrier wave. Also, the chirp is not limited to linear frequency sweep, but can sweep non-linearly. However, due to the advantages of the linear frequency sweep, this type is used in the examples, for illustrative purposes. Similar to previously described example methods, an advantage of the present example method is that it can be employed to generate an arbitrary number of mismatched coded waveforms with identical length (duration) and frequency range. However, the method is not restricted to be used only for identical length and frequency range. The examples presented here are provided to demonstrate this capacity and therefore identical length (duration) and frequency range are used. It will be understood that mismatched coded waveforms with dissimilar lengths and/or frequency ranges may also be employed.

A new coded waveform generated according to the present example method may appear to lose the main advantage of Golay Codes, which was being sidelobe free. However, by using Golay Codes with different number of bits (i.e. Golay Codes with different numbers of bits, but with an equal total code length, where the total code length will be adjusted by the length of the chirp inserted in each bit) and introducing chirps in those bits, new mismatched coded excitations are produced. In this case, although the slopes of frequency modulations (FMs) in different parts of the combined frequency-modulated Golay Codes (GC-FM) are identical, the complementary property of Golay Code is used to cancel the sidelobes.

This example method may be compared with the first example method that was described above (mismatched code generation employing multiple dissimilar chirps per coded waveform). In the first method, it was required that the slope of any of sub-chirps (chirps within a given time division) vary from the other chirps in the same coded waveform, as well as any part of the other coded waveform (where positive and negative slopes with the same value are considered different). In combined frequency modulated Golay coded waveforms generated according to the present example embodiment, the slope of chirps varies among different coded waveforms, but not within the same coded waveforms. The slope of the chirps is common within one combined frequency modulated Golay code, such that the property of complementary codes when their matched filters are added together, will cancel the extra peaks produced.

Figures 11A, 11B:
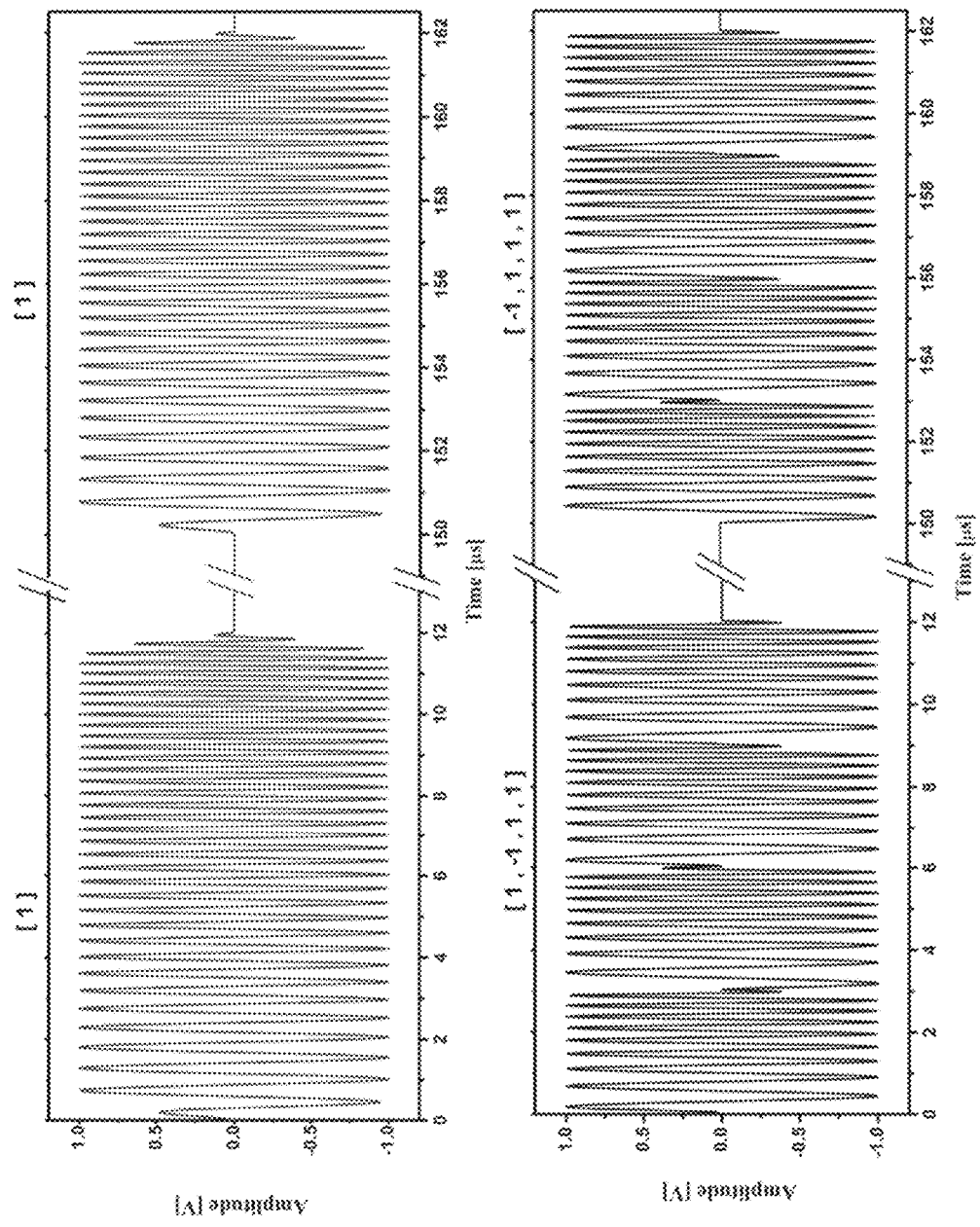
FIGS. 11A and 11B plot examples of combined frequency-modulated Golay Codes (GC-FM) employing chirped Golay Codes, where (A) illustrates a waveform with an FM chirp of 12 μs duration and frequency range 1.6-4.3 MHz, transmitted again after 150 μs, and (B) illustrates a 4-bit Golay Code with carrier waveform of a 3 μs FM with similar frequency range as (A), and where after 150 μs, the complementary combined GC-FM is transmitted.

The proposed method can be explained by an example. FIG. 11A shows a chirp of 12 μs duration. As shown in the figure, the same chirped signal can be transmitted again after detecting the response to the first coded waveform, for instance, after 150 μs. As such, each chirp can be considered as a 1-bit Golay Code with complementary parts of [1] and [1].

FIG. 11B illustrates an example of a 4-bit Golay coded waveform that is chirped according to the present example method (the complementary coded waveform is not shown). For example, a 4-bit code may have bit values of [1,−1,1,1], with complementary code bit values of [−1,1,1,1]. If the duration of the signal is fixed to 12 μs, a chirp introduced as the carrier waveform of Golay Code results in the combined Golay Code and FM shown in FIG. 11B. The complementary code is produced similarly.

Figure 12:
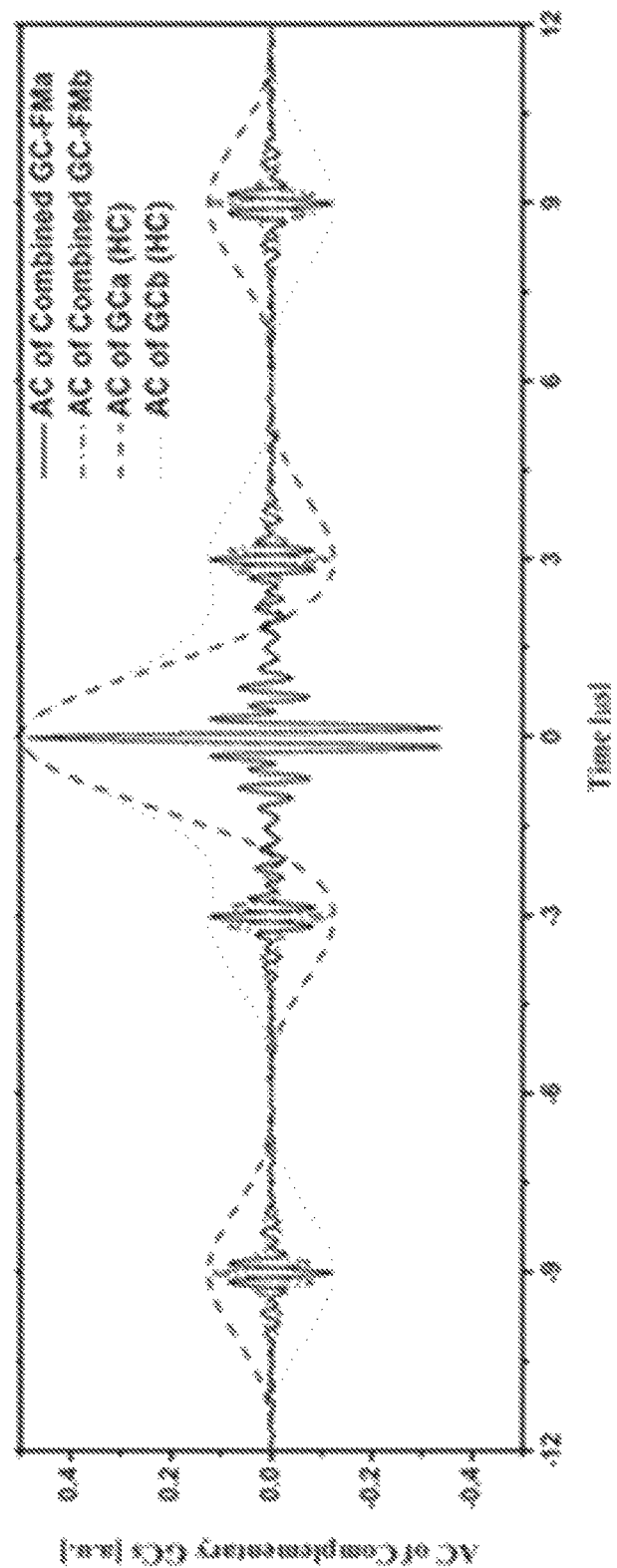
FIG. 12 plots the pulse compression of complementary combined GC-FMs (FIG. 11B) and a conventional half-cycle 4-bit Golay Code, where the autocorrelation of each part of the combined GC-FM generated sidelobes that are out of phase with the other autocorrelation, and therefore, similar to a conventional Golay Code, sidelobes cancel each other. (AC: autocorrelation)

FIG. 12 compares the autocorrelation of the complementary parts of the combined GC-FM with a conventional Golay coded waveform which has a half-cycle sinusoidal carrier with 6-μs period in the absence of chirp. It shows that the complementary parts generate out-of-phase sidelobes. In the figure, AC indicates autocorrelation, GC-FMa and GC-FMb are the complementary parts of the described 4-bit combined GC-FM (the GC-FMa is shown in FIG. 11B), and GCa and GCb are the complementary parts of the mentioned half-cycle (HC) sinusoidal Golay coded waveforms. As shown in the figure, matched filtering of each part of the combined GC-FM generates a main lobe and several sidelobes very similar to a conventional Golay Code. Nevertheless, the sidelobes cancel each other out when the autocorrelations of the complementary parts are added together.

Figure 13:
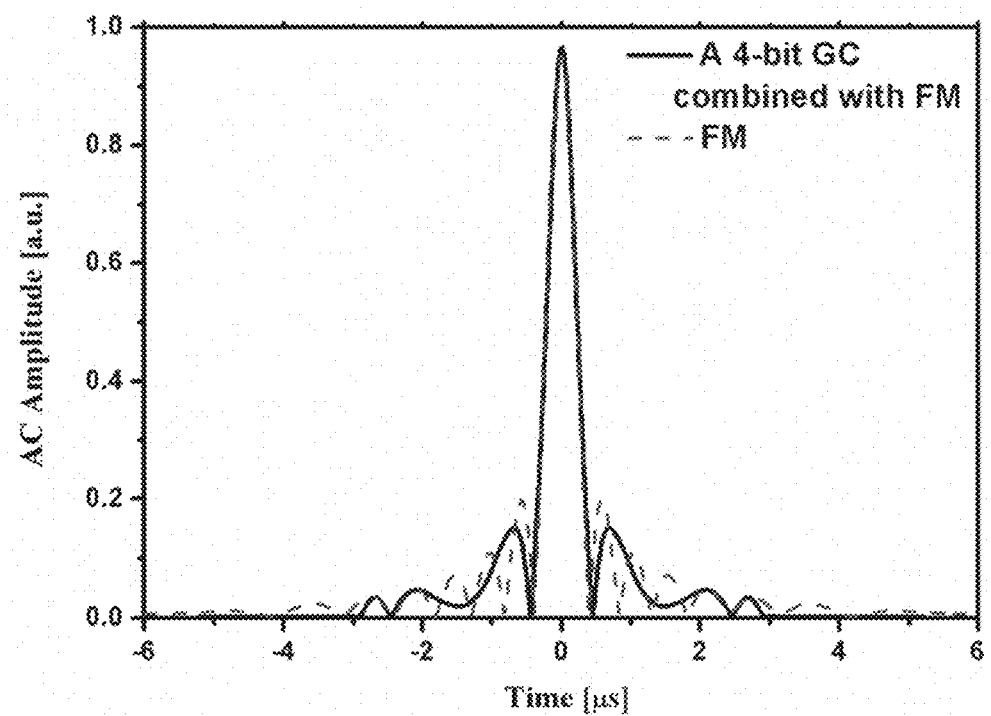
FIG. 13 plots the results of pulse compression for FM in FIG. 11A and combined GC-FM in FIG. 11B, where the complementary pulse compressions are added together and then enveloped.

The final pulse compression of the GC-FM is shown in FIG. 13 and it is compared with the pulse compression of a chirp (FIG. 11A). The main result is that the combined GC-FMs are mismatched among themselves.

As mentioned in the combined GC-FM, the slope of chirps should be different among different mismatched coded waveforms. According to one example implementation, this can be assured by using Golay codes with a different number of bits while fixing the total length of the waveform (that is, the length of the combined GC-FMs), which will change the duration of sub-chirps from coded waveform to coded waveform. Therefore, other combined GC-FMs can be produced in the same manner by employing Golay Codes with 2, 8, 10, 16, 26 bits and so on.

Another example implementation for generating slopes of sub-chirps that vary from mismatched coded waveform to mismatched coded waveform is to use different frequency modulations, as introduced in the first method described above. One simple example is to use increasing (FM1) and decreasing chirp (FM2) sequences and combine them with Golay codes. If it applied to combined GC-FMs with 1, 2, 4, 8, 10, . . . bit Golay codes, it readily generates another set of combined GC-FMs.

In general, if FM1, FM2, . . . FM7 in FIG. 4 (and other mismatched FMs generated similarly, for instance the ones in FIG. 6) are all combined with the same 4-bit Golay code, to generate a new set of combined GC-FM codes, the resulting combined GC-FMs will be mismatched (the original FMs are assumed to be mismatched).

In one example embodiment, mismatched coded waveforms may be generated by using mismatched FMs and employing them as the carrier waveform of Golay codes, which can be used to generate multiple new mismatched coded waveforms. However, in this case, it is not correct to assume that the resulting coded waveforms are automatically mismatched. In the preceding examples, when different Golay codes were used with one chirp, like FM1, or when different mismatched FMs were used with one Golay code like a 4-bit Golay code, the results were automatically mismatched. If two such sets of coded waveforms are combined together, one should determine whether or not the slope or slopes of chirp or sub-chirps inserted in any Golay code is unique within the set of mismatched coded waveforms. In other words, a given slope should only be used for one combined GC-FM.

In another example embodiment, a new mismatched coded waveform can be generated by concatenating two or more mismatched combined GC-FMs. Such a method of concatenating mismatched coded waveforms will generate new longer coded waveforms, and this method can be used to generate mismatched coded waveforms. Therefore, by concatenating the mismatched coded waveforms generated with methods mentioned we can generate new longer coded waveforms, they will be mismatched with any other coded waveform generated if the slopes of the sub-chirps remain unique to one FM-GC.

The mismatched coded excitations that can be generated according to the example methods described herein may find application in a wide variety of fields, including 3D ultrasound imaging and imaging applications that employ transducers with thousands of elements.

Functionally Encoding of the Signals

As described above, the use of mismatched coded waveforms enables distinguishing the source of simultaneously transmitted signals. This capability can be used to functionally encode the transmitted signals. One example application in which mismatched codes may be employed is multiple wavelength photoacoustic probing/imaging. If the transmitted stimulations from several lasers are encoded using mismatched waveforms, the receiver can separate the responses induced by each of the waveforms as if they were transmitted independently.

The systems and methods disclosed herein can be employed to facilitate simultaneous detection signals produced by two different excitation modalities, such as, but not limited to, photoacoustics and ultrasound.

In some embodiments, the coded excitation and the detected energy may be different modalities. For example, the coded excitation may be optical, while the detected energy may be acoustic (photoacoustic imaging).

In one example embodiment, the excitation energy may be generated according to different modalities. For example, the coded excitation energy may be both optically and acoustically generated. For example, a photoacoustic signal may be generated by emitting laser light onto a sample, and ultrasound may be generated via insonification with ultrasound. These modalities may use the same detector, for instance, an ultrasonic array transducer, since the ultrasound energy is responsively generated in both cases. By using mismatched coded excitations for intensity-modulated emitting laser and for transmitting ultrasound, the receiver will be able to discriminate the sources of the simultaneously transmitting signals. It is noted that due to the very strong response of ultrasound compared with a photoacoustic signal, it may be beneficial to use different frequency range and excitation durations.

In some embodiments, there may be a small cross-correlation among the mismatched codes that can be reduced with increasing the signal duration. Several other techniques can be also applied to reduce the cross-correlation between proposed mismatched signals.

The following four example methods provide illustrative and non-limiting example of additional approaches that can be employed to further reduce the cross-correlation. Each of these example methods require consecutive transmissions and measurements, (i.e. these techniques require multiple transmission and detection to perform averaging and reduce the artifacts).

In one example, the starting phase of some of the signals can change irregularly in consecutive transmissions: In another example, the starting time point of some transmitted signals can move irregularly in consecutive transmissions. In applications involving multi-element transducers, different combinations of the elements can be employed for the transmission, thus, in each consecutive transmission the locations of the adjacent signal sources move. In yet another example, the transmitted coded waveforms can switch between the elements or change in each transmission.

Each of these example methods either moves or changes the cross-correlations in each consecutive insonification. Therefore, the artifacts move or change with each measurement and reduce when averaged over several measurements. The processed signals (autocorrelations) are not affected by these techniques, as long as the pulse compressions are calculated with the corresponding transmissions.

Another method of reducing the correlation between coded waveforms in successive multiple transmission is the use of Hadamard matrix. Hadamard decoding has been used widely to decode different codes with correlation among themselves (Chiao, Thomas, and, Silverstein, IEEE Ultrasonics Symposium 1997) (Misaridis and Jensen, Ultrasonics. 2002; 40: 593-597) and similarly can be used for reducing the small correlation among the mismatched codes presented here.

As noted above, these example systems and methods provided herein can be employed for high frame rate ultrasound imaging. It will be understood, however, that the systems and methods provided herein may be adapted to and/or employed for a wide variety of applications, such as, but not limited to, radar, sonar, NDT ultrasound, photoacoustic imaging and characterization, MRI imaging and communication systems.

The following examples are presented to enable those skilled in the art to understand and to practice embodiments of the present disclosure. They should not be considered as a limitation on the scope of the disclosure, but merely as being illustrative and representative thereof.

EXAMPLES

Example 1

Experimental Demonstration of Spatial Encoding of Signals Using Mismatched Codes For example, elements of a transducer array may be configured to transmit mismatched codes (mismatched coded waveforms) simultaneously, and the receiver elements can detect the source of each signal and, therefore, calculate the distance that the signal passed through.

Figure 14A:
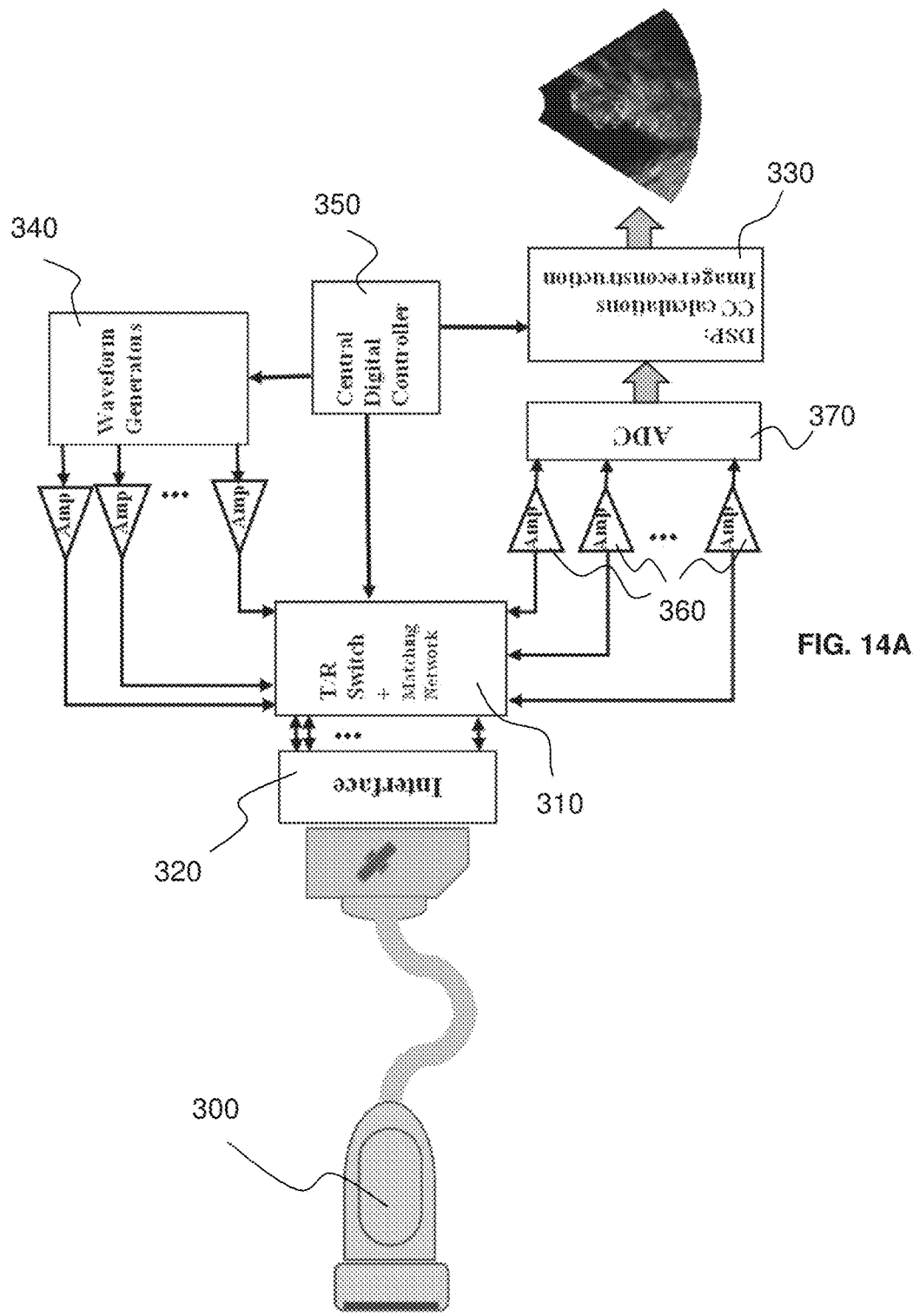
FIGS. 14A-C illustrates (A) a block diagram of an example system for performing coded excitation imaging according to various methods of the present disclosure, (B) a schematic of the simultaneous transmitted mismatched codes from 5 elements, and (C) an ultrasound image generated by superposition of five separate images generated by transmission in scheme shown in (B).

FIG. 14A is a block diagram illustrating an ultrasound imaging system configured according to the example methods described above. A phased array ultrasound transducer 300 was connected to a series of multiplexers or T/R switches 310 through an interface connection 320. The T/R switches 310 were used to control the connection of the array elements either to the acquisition boards 330 or waveform generators 340. The switches or multiplexers 310 were controlled by central digital controller 350. The response to each set of insonification is collected by the whole array or a sub-array of elements of ultrasound transducer 300.

The required multiple mismatched codes were generated in the LabView program (NI, Austin, Tex., USA) for simulations as well as experiments using the sampling frequency corresponding to the hardware. The simulations were also performed with Matlab (MathWorks, Natick, Mass., USA). It will be understood by those skilled in the art that these codes can be generated similarly using any other programming language, such as C++. All of them were generated using LabView for experiments and simulations, and most of the simulations were also performed with Matlab.

The mismatched codes were either fed to waveform generator instruments (33500B, Agilent Technologies Inc., Santa Clara, Calif., USA) or generated in real time by a LabView program and converted to analog signal through digital-to-analog convertor (NI PXI-5442, TX, USA). Each transducer was fed with a dedicated coded waveform, such that the coding was spatial coding.

The acquisition signals were first amplified through amplifiers 160 and then digitized through analog-to-digital converters 370 (PXI-5105, NI). An in-house developed LabView program (NI) was used to control the process. The program also calculated the cross-correlation functions by matched filtering with corresponding reference signals. In the case of mismatched codes based on Golay Code, the complementary matched filters were added to generate the final time domain signal.

Each transmitted code generated a set of cross-correlation signals. These signals were used to generate a low-resolution image. Different algorithms can be used for image reconstruction; the most common method is beamforming which uses delay and sum method. In the present example case, an algorithm and formulation described by Jensen et al. was employed (Ultrasonics J. 2006; 44: p. e5-e15). It will be understood by those skilled in the art that other image processing and image reconstruction methods can be readily employed. The final image was reconstructed from superposing all low-resolution images.

Figure 14B:
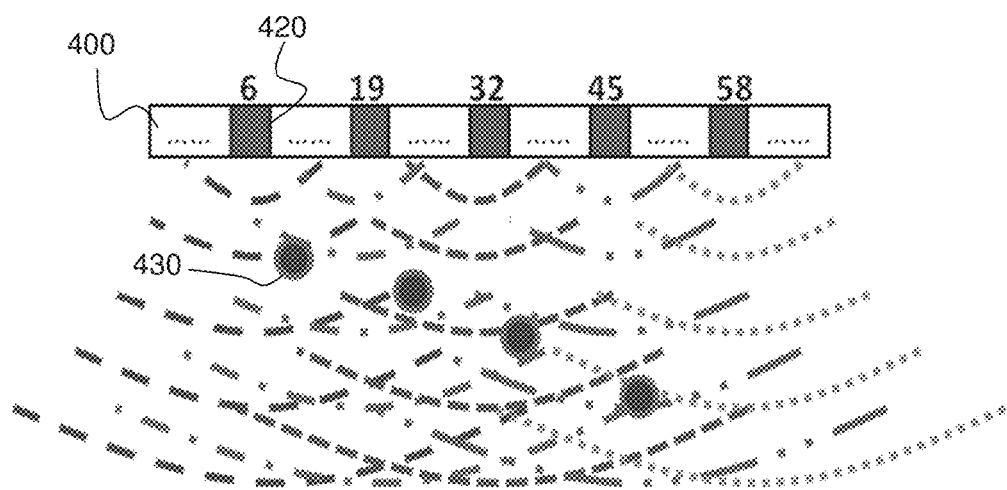

In the present example implementation, the number of simultaneously transmitted mismatched codes was limited by number of available waveform generator channels, which was five channels. FIG. 14B illustrates the configuration of the system such that a set of 5 transducer elements were simultaneously fired (420 in FIG. 14B). The transmit elements were #6, 19, 32, 45, and 58 which were used to insonify the field. The last four elements were stimulated by two dual-channel analog waveform generators (33500B). Element 6 was stimulated by a function generator (FG) board PXI-5442 (NI) which was also used as the master board. The analog function generators as well as the data acquisition card were initiated by the output external trigger of the master function generator board (PXI-5442). No power amplifier was used to boost the transmission signals. The sample was four ~1 mm wires (430 in FIG. 14B) with approximately 3-mm distance in-between. The wires were held in a water tank in front of the transducer array.

Figure 14C:
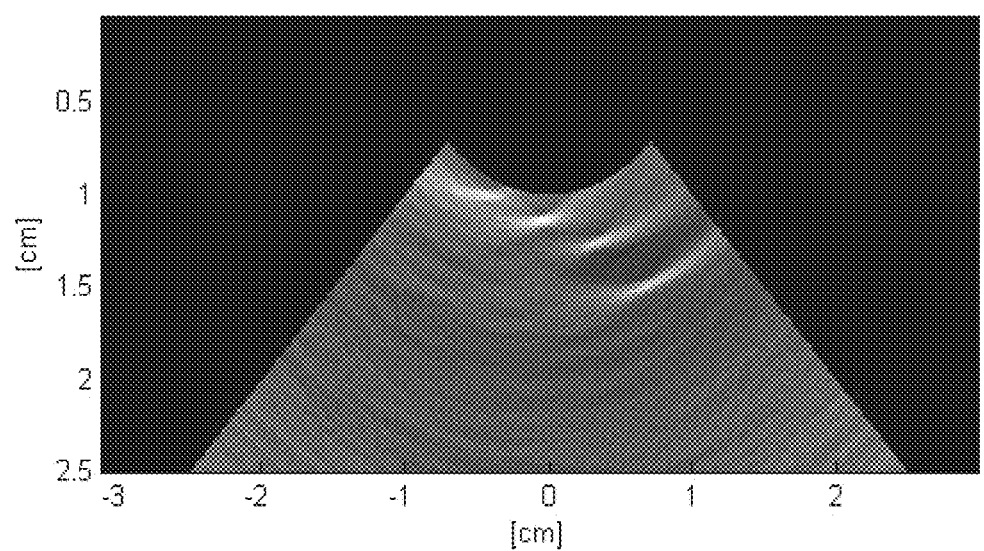

Long 2-ms codes of a very low amplitude signal of 20 $mV_{pp}$ were used in the transmission. The five mismatched codes that were employed were sinusoidal chirps with a frequency range of 1 to 5 MHz and sweep patterns similar to FM1 to FM5 introduced in FIG. 4. The detected signals from 59 elements (400 in FIG. 14B) of the array were used to calculate the cross-correlation signals with these five FMs and, therefore, to generate five low-resolution images corresponding to each transmitting element and code. Combining these images, the final image was produced and is shown in FIG. 14C (generated by transmitting five mismatched codes). It will be understood that this configuration was employed for practical purpose and is not intended to illustrate an inherent limitation of the present embodiments.

Figure 15A:
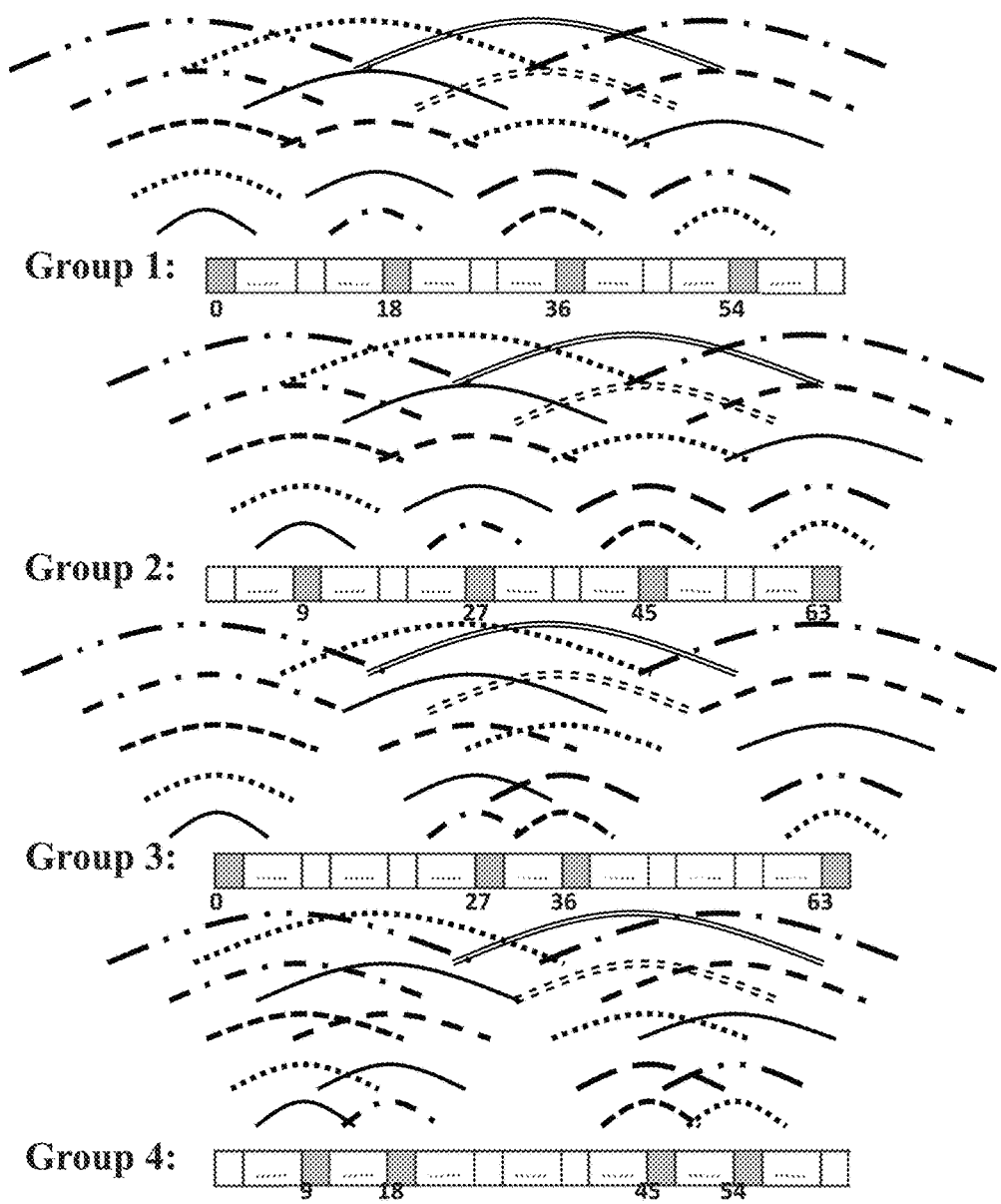
FIGS. 15A-C illustrates (A) the waveform transmission scheme. The transmitting elements are demonstrated by filled elements, where all other elements were employed in receiver mode; (B) ultrasound Image of 8-wires generated with FM sequences described in the table shown in FIG. 17A; and (C) ultrasound Image of 8-wires generated with combined GC-FM sequences described in FIG. 17C. The arrows show the locations of the wires.

In another experiment, four other multiplexers were added to switch the transmitting/receiving elements. Eight elements of the array were selected and connected to these four multiplexers. These multiplexers were used to switch between the eight elements, thus, at any given time, four elements could perform as transmitters and the other four as receivers. Only the two dual-channel analog waveform generators were used to perform four simultaneous transmissions with voltage of 10 Vpp (no power amplifier used). The schematic of the signal transmission is depicted in FIG. 15A.

The eight elements used in transmission mode were 0, 9, 18, 27, 36, 45, 54, and 63. These elements were switched between transmit and receive modes in four different groups.

In this experiment, the duration time of the transmitted codes was reduced to 12 μs. As a result, when the elements were receiving the signal from typical depths (the typical depth depends on the application, for instance in biomedical imaging, the typical depth can be few centimeters, this can be more accurately specified by specifying the subject), the simultaneous transmissions did not interfere due to transducer crosstalk.

For the planned experiments and focal distance of the array, the signal acquisition process does not require more than 150 μs to receive the response from the farthest objects. This short interval between transmissions enables a very high speed signal acquisition (667 Hz) and, therefore, facilitates performing averaging over the responses. For instance, when the transmitted signal from one element is fixed, the phase or starting time or the waveform of an adjacent transmitted signal can vary. As a consequence, the cross-correlation between each pair of the transmitted signals diminished with averaging.

Two sets of waveforms were considered in the experiments: first, a set of mismatched chirps and then, a set of combined GC-FM. The mismatched chirps were generated using the sweep patterns shown in FIG. 4: FM1 to FM4 and FM7 with identical duration of 12 μs. Also, all the FMs share the same frequency range of 1.6-4.3 MHz.

To perform effective averaging that diminishes the artifacts, each element transmitted ten successive coded excitations in every 150 μs. The sequences of FM signals for four simultaneous transmitting elements are described in FIG. 17A. The location of transmitting elements was then permuted in four groups as depicted in FIG. 15A and the same sequences were repeated with the next layout of elements.

Using five different FMs provided a large number of possible permutations. Thus, the adjacent waveforms varied in each transmission (technique 4). The '*' sign in the table indicates that the phase of the coded excitation was changed by 180° (technique 1).

The abovementioned scheme was used to generate an US image of eight wires (~1 mm diameter). Four simultaneous elements were used to transmit coded excitations. One set of detected signals was collected as a result of these simultaneous transmissions. The pulse compressions were performed with corresponding transmitted signals, and that yielded four low-resolution images.

Afterwards, the transmitting elements were changed, and a new set of received signals was collected. This process was repeated for the four implemented groups (FIG. 15A). Therefore, four sets of data were collected with four groups of transmission. Each group of the transmissions was consisted of four simultaneous transmitted elements (FIG. 15A). Each element transmitted 10 successive codes in total time of 150 ms (each signal was 12 μs but transmitted every 150 μs). The codes were selected in a way that not only the simultaneously transmitting codes are mismatched (spatial encoding) but also subsequent codes were also mismatched (temporal encoding). Although long delays exist between the codes in the example, temporal correlation between the codes were not a concern.

After collecting the data, the processing was performed with the following steps:

Step 1: For Group 1: The transmitted elements and the code sequences fed to each of the transmitted elements are known. All receiving elements (assuming Nr) were cross-correlated with the four sequences of 1.5 ms of transmitting signals. This resulted in 4×$N_r$ cross-correlation signals. Here the averaging process has been performed automatically, by calculation of the cross-correlation with 1.5 ms total reference signal and of each 150 μs separately and averaging afterwards).

Step 2: Each $N_r$ set of cross-correlations with one transmitted set of signals (from one element) can be used to generate a low-frequency image. The location of the transmitter is known and the location of the receiver as well, therefore using an image reconstruction algorithm (e.g. the example method referred to above) results in one image of the field. Therefore, four low-resolution images were generated from Group 1.

Step 3: Step 1 and 2 are repeated for Groups 2 to 4. Thus, sixteen low-resolution images were produced.

Figure 15B:
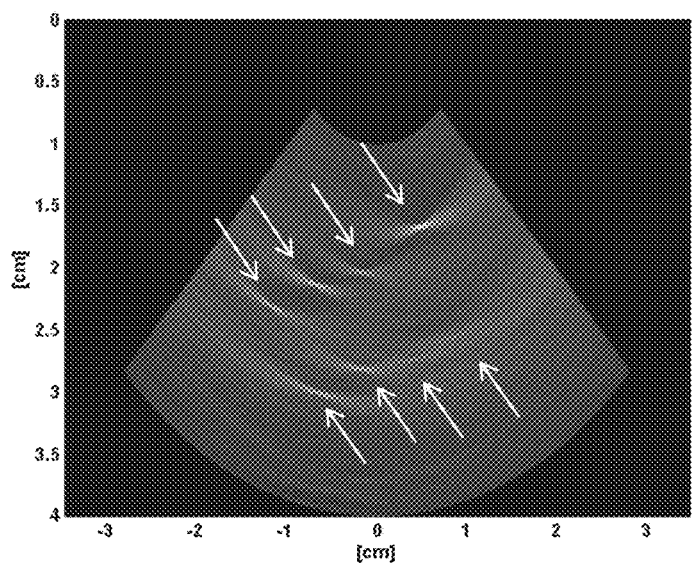

Step 4: Superposition of the sixteen images resulted in one final high-resolution image, shown in FIG. 15B.

It will be understood that the aforementioned method of initially generating low-resolution images, and subsequently processing the low-resolution images to obtain a high-resolution image, is but one example implementation of a method of processing the various cross-correlations (for the different codes and different elements) in order to produce an image. For example, in an alternative example embodiment, the various cross-correlations may be processed (based on the known timing of the excitation codes provided to the transducer elements) to obtain a final image without producing intermediate low-resolution images.

In another experiment, the application of combined GC-FM signals for simultaneous multiple transmissions was investigated. Four different Golay codes with 1, 2, 4, and 10-bit lengths were used to generate combined codes (FIG. 17B). The combined GC-FMs generated with the above-mentioned GCs were labeled CGC1, CGC2, CGC4, and, CGC10, respectively.

The sequences for four simultaneous transmissions are shown in FIG. 17C. CGC1 and CGC4 were the combined GC-FMs shown before in FIG. 11A and FIG. 11B, respectively. CGC2 and CGC10 were also generated similarly by combining 2 and 10-bit Golay codes with up-chirping FM1 (FIG. 4). The combined GC-FM codes used in this example (FIG. 15C) all had identical total code length of 12 μs (e.g. FIGS. 11A and B), using the same bandwidth and dissimilar Golay code bit numbers, the slopes of the codes in different combined GC-FM codes were automatically different, therefore the codes were mismatched.

It is noted that it is possible to use any other FM to generate more mismatched waveforms, for instance, down-chirp: FM2. The reverse sweep FM2 had also been used for some of the codes that were marked with 'r' superscript in FIG. 17C. Also, out-of-phase signals were marked with a '*' sign as before, here only used for CGC1.

In the experiment, the sequence of five consecutive composite GC-FMs was launched first, followed by the respective complementary codes as shown in FIG. 17C. The sequential insonifications were performed every 150 μs. As in the previous case, each group generated four simultaneous transmissions. The collected response signals were divided into two parts corresponding to the response to two complementary Golay codes.

Figure 15C:
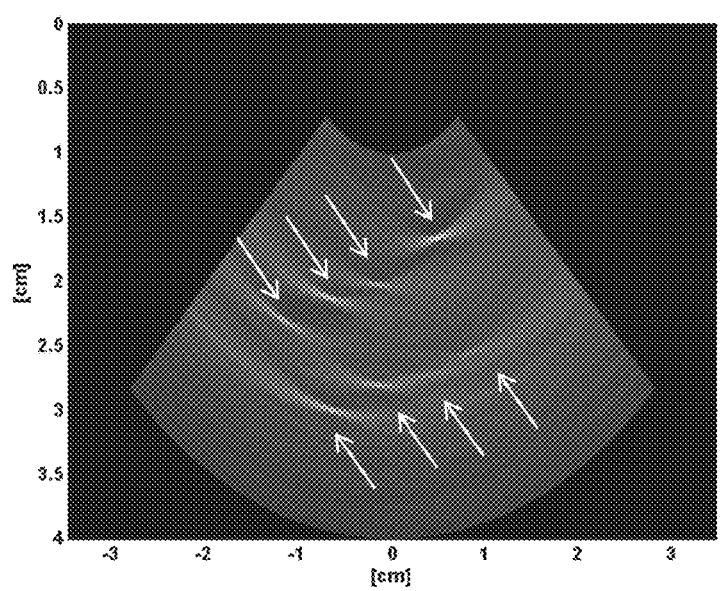
Figure 16A:
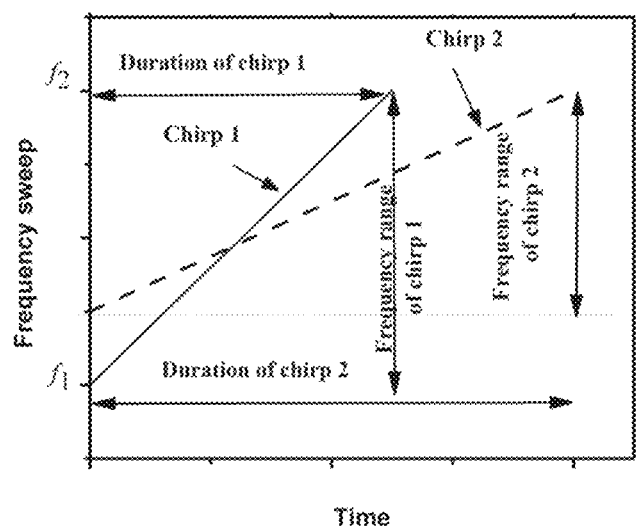
FIG. 16A-B illustrate (A) generating chirps with dissimilar slopes by employing different frequency ranges and code durations (Misaridis, and, Jensen, IEEE Trans. Ultrason., Ferroelect., Freq. Contr. 2005: 52(2), 207-218.); and (B) a method for generating multiple mismatched chirps with the same bandwidth and duration. (El-Khamy, S. E., Shaaban, S. E., and Thabet, E. A., IEEE 4th International Conference on Spread-Spectrum Systems and Techniques (ISSSTA\'96). 1996; 1209-1213). This method generates non-uniform resolution and signal-to-noise ratio.
Figure 16B:
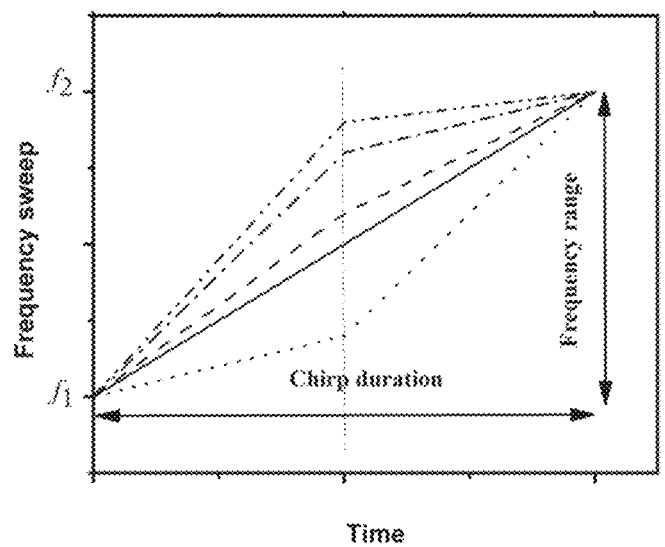

In a manner similar to processing a conventional Golay code, each part was matched filtered and then both parts were added together to produce the final signal. Each set of collected data generated four sets of pulse compression signals corresponding to the transmitting elements. These signals were used to produce four low-resolution images and a total of sixteen images for all groups. The final high-resolution image was generated through direct superposition of the sixteen low-resolution images and is shown in FIG. 15C.

Example 2

Functional Imaging

The examples of functional imaging presented here were based on two mismatched frequency modulation codes of up-chirp and down-chirp. However, it will be understood that the methods provided in the present example can be readily adapted to employ any of the mismatched coding methods disclosed above.

Figure 18:
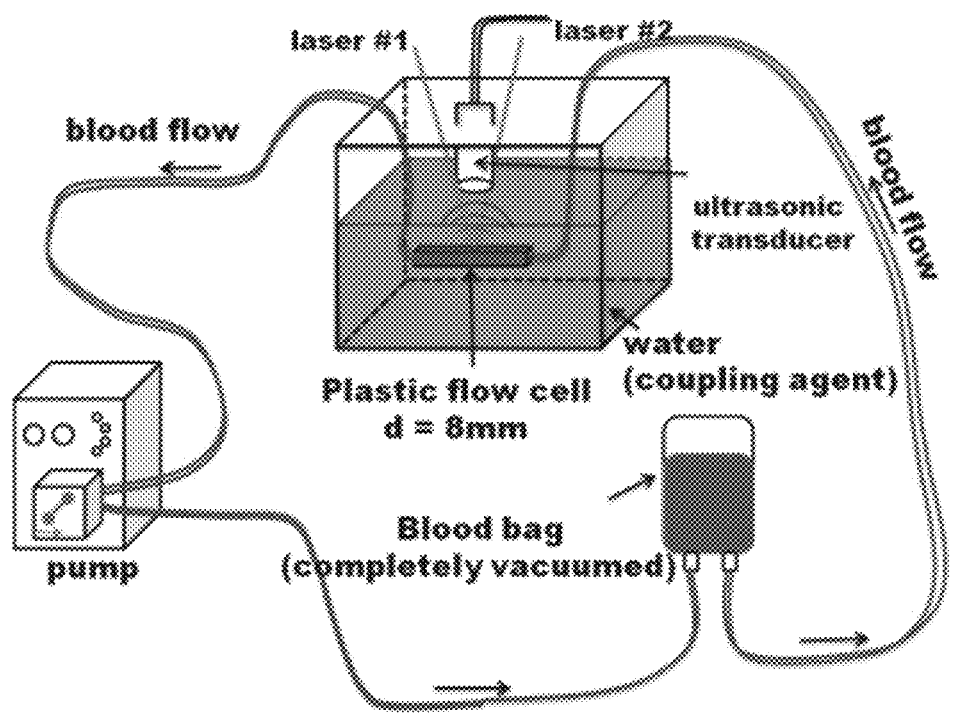
FIG. 18 is an illustration, of a system including a blood circulation apparatus and photoacoustic radar probing apparatus.

The feasibility of simultaneous dual-wavelength photoacoustic (PA) probing is demonstrated for oxygen-saturated and deoxygenated sheep blood. Two continuous wave (CW) lasers were employed; an 805 nm diode laser (Laser Light Solutions, NJ, USA) and a 680 nm diode (LDX Optronics Inc., Maryville, Tenn., USA). The 680 nm diode laser was modulated by a high-frequency driver VFM5-25 (MESSTEC, Germany) and the 805 nm diode laser was equipped with its own driver. A dual-channel arbitrary waveform generator (33500B, Agilent Technologies, Inc., Loveland, Colo., USA) was used to control the drivers. The experiment was performed on a blood circulating rig (FIG. 18). A peristaltic pump (Heidoiph Instruments GmbH & Co., Germany) was used to circulate heparinized sheep blood (Caderlane Labs, Burlington, ON, Canada) continuously from a sealed blood bag to a convertible flow cell (CF-CAS0004, IBI Scientific, Peosta, Iowa, USA) and back to the blood bag through plastic tubing. The output fibers of the two diode lasers were connected to two identical 0.8-mm collimators (F230SMA-B, Thorlabs, NJ, USA) which were directed toward the same point on the surface of the measurement unit. The area of the 805-nm laser beam was adjusted with a lens to cover approximately the same area on the surface as the 680 nm laser beam (~15 mm diameter). A focused ultrasonic transducer with 1-MHz center frequency V314 (Olympus NDT Inc., Panametrics, USA) was placed in front of the measurement cell at its focal distance, 1.9 in. The output signal of the transducer was amplified 40 dB (preamplifier 5676, Panametrics, Olympus, USA) before being digitized by a data acquisition card. Signal acquisition and synchronization were performed through a National Instruments system.

First, the blood was exposed to ambient air to become fully oxygen saturated. The laser powers were set to 900 mW (680 nm) and 600 mW (805 nm). The driver of the 680 nm laser was set to an up-sweeping chirp from 300 kHz to 1.3 MHz, and the 805 nm laser was set to down-sweeping the same frequency range. The chirp duration was set to 1 ms and the received signals were averaged over 50 measurements. Thus the total exposure time for each measurement was 50 ms. Both channels of the waveform generator were synchronized with an external trigger generated by the National Instruments system. The photoacoustic measurement was subsequently performed three times, once with each laser and the third time with both lasers operating simultaneously.

Figure 19:
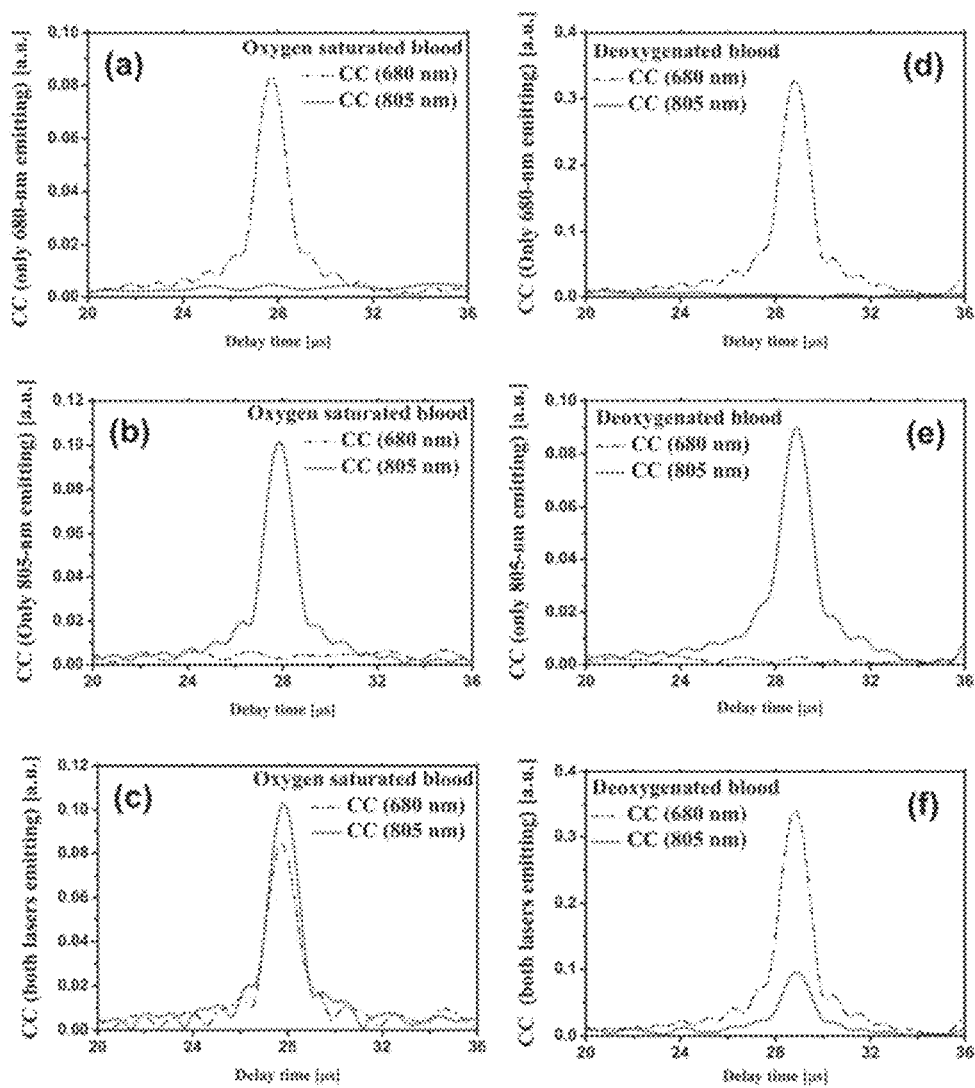
FIGS. 19A to F show photoacoustic cross-correlation (CC) signals from oxygen saturated blood with irradiation of (A) 680 nm, (B) 805 nm, and (C) both wavelengths. Also shown are cross-correlation signals from deoxygenated blood with irradiation at (D) 680 nm, (E) 805 nm, and (F) both wavelengths. When one laser is off, its corresponding CC in the figure shows the cross-correlation of the associated (up- or down-swept) chirp with the detected signal. These CCs experimentally demonstrate the correlation of the two mismatched chirps.

FIG. 19 (a) to (c) show the envelope cross-correlation signals of three measurements; (a) 680 nm irradiation only, (b) 805 nm irradiation only, and (c) both lasers emitting together. Comparison between the peak values in the dual-waveform case with each individual waveform (when the other laser was off) shows that each signal operates independently of the other signal with minor interaction between them.

The variation of peak values in the dual-waveform case compared with the single waveform measurements are −36.8 dB and −43.8 dB for 805 nm and 680 nm wavelengths, respectively. This variation is smaller than the noise level in each single wavelength measurement. On the other hand, the cross-correlation of each signal with the other linear frequency modulation chirp generates a baseline less than −22 dB (FIGS. 19 (a) and (b)). It should be noticed that this baseline due to the cross-correlation between the two waveforms depends on bandwidth and chirp duration. With these parameters increasing, it is possible to decrease the baseline level. Using the molar extinction coefficients of hemoglobin in the employed wavelengths (W. G. Zijlstra, A. Buursma and O. W. van Assendelft, "Visible and Near Infrared Absorption Spectra of Human and Animal Haemoglobin: Determination and Application", Boston: VSP, 2000.), the measured data can readily reveal the hemoglobin oxygen saturation.

By adding sodium dithionite to the oxygenated hemoglobin, one can increase the level of deoxygenation in the blood (K. B. Saebvarnothing, A. Bjvarnothingrnerud, Proc. Intl. Soc. Mag. Reson. Med., 8, 2025, 2000). About 0.4 g of sodium dithionite powder (Sigma-Aldrich, St. Louis, Mo., USA) was added to 150 ml of the blood in the container which is enough to completely deoxygenate the blood.

After 20 minutes as blood circulating through the tube loop, the experiments were repeated. The laser power, chirp duration and number of data acquired for averaging were the same as for the first experiment. The envelope cross-correlation signals are shown in FIG. 19 (d) to (f) for 680 nm, 805 nm, and simultaneous operation of both lasers, respectively. The variation of peak values in the simultaneous and single wavelength measurements are −24.6 and −28.2 dB for 805 nm and 680 nm operation, respectively. The baselines due to cross-correlation with the other chirp are seen in FIGS. 19 (d) and (e) and are −5.7 and −27.4 dB, respectively. These small variations confirm that the simultaneously transmitted mismatched codes generated independent responses that were accurately measured.

Figure 20:
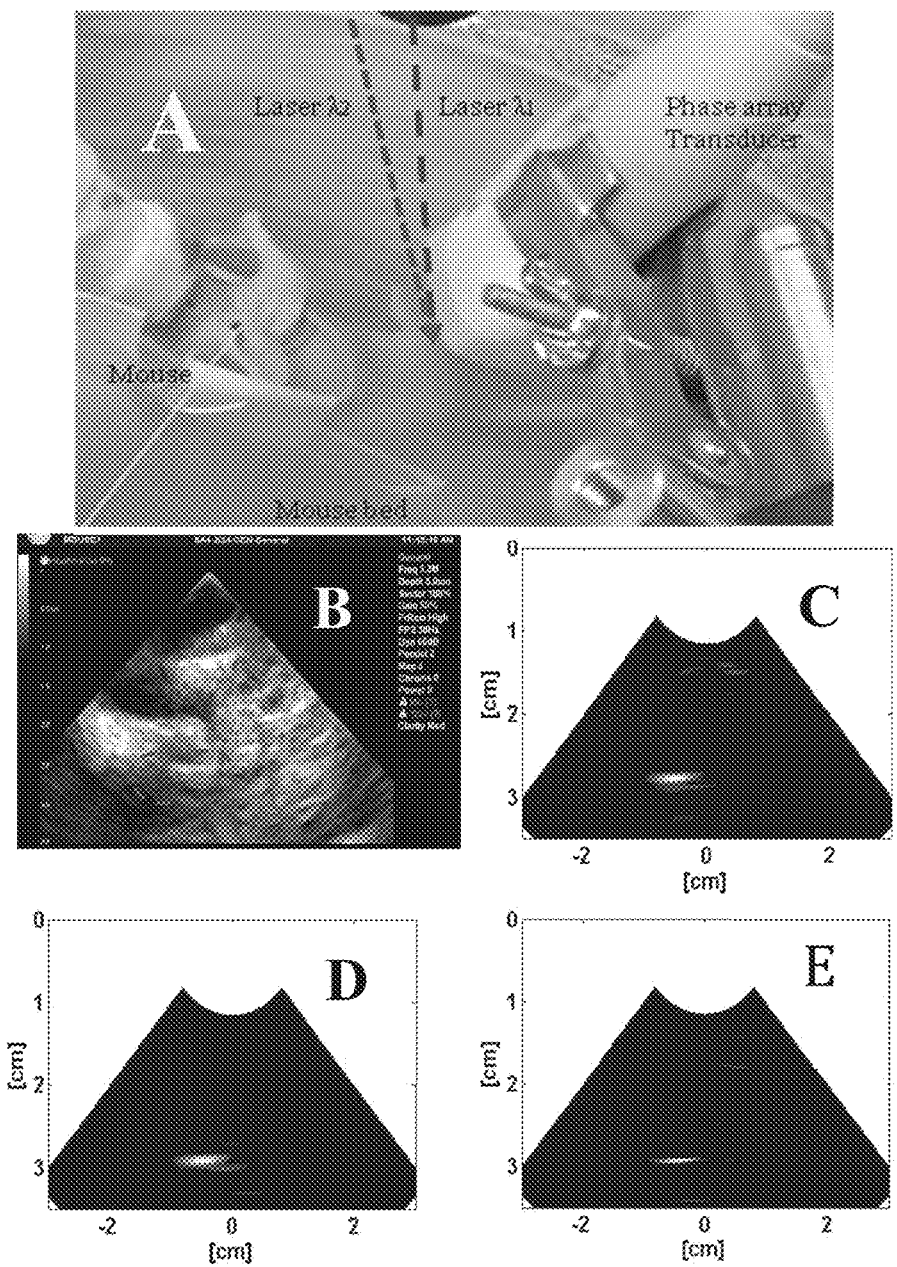
FIGS. 20A-E provide results from photoacoustic imaging of cancerous tumor in mouse thigh, showing (A) mouse leg and transducer are placed inside the water tank and the laser beams emit from the top; (B) an ultrasonic image of the mouse thigh using a commercial ultrasonic system; (C) a photoacoustic image obtained with the 805-nm laser only; (D) a photoacoustic image based on the 805-nm laser modulation waveform with both lasers emitting simultaneously; and (E) a photoacoustic image based on the 680-nm waveform with both lasers emitting simultaneously.

In another experiment aiming at extending the proof of the validity of the line scan results of FIG. 20 to full multi-wavelength photoacoustic images, dual-wavelength photoacoustic probing was applied for in-vivo imaging of a cancerous tumor in a mouse thigh. A nude mouse was purchased from Charles River Laboratories Inc. (MA, USA). Cultured FaDu cells (human hypopharyngeal head-and-neck squamous cell carcinoma) were injected 21 days prior to the experiment in the right thigh of the mouse. This experiment was performed under the guidelines of animal protocol 20010465 approved by the Division of Comparative Medicine (DCM) of the Faculty of Medicine at the University of Toronto. Animal handling was performed according to the guidelines for the care and use in the laboratory. The animal was anesthetized using isoflurane gas and full anesthesia was maintained throughout the experiment by administrating 1.4 L/min oxygen and 1 L/min isofluorane. An infrared (IR) lamp was also used to keep the animal body temperature at a constant level.

The photoacoustic imaging of the mouse thigh was first performed by an in-house imaging system described elsewhere (S. Telenkov, R. Alwi, A. Mandelis, and A. Worthington, "Frequency-domain photoacoustic phased array probe for biomedical imaging applications," Opt. Lett., vol. 36, no. 23, pp. 4560-4562, 2011.). A 64 element phased array ultrasonic transducer SA4 2/24 (Ultrasonix, BC, Canada) was used. The same laser diodes emitting at 805 and 680 nm were employed with respective powers of 3 W and 1.3 W. The mouse leg and the transducer surface were fully submerged in water for acoustic coupling (FIG. 20A). Photoacoustic imaging was first performed using the 805 nm laser alone and then using both wavelengths emitted simultaneously. After photoacoustic imaging as the transducer was fixed in the water tank, its interface was detached from the photoacoustic imager and was connected to a commercial ultrasound system (Ultrasonix, BC, Canada) to perform ultrasonic imaging for comparison.

The photoacoustic images were reconstructed using a phased-array reconstruction algorithm modified for photoacoustics (Jensen, Nikolov, Gammelmark, and, Pedersen, Ultrasonics J., 44, e5-e15, 2006). The ultrasonic image of the mouse thigh and tumor as well as PA images with 805 nm (emitted alone) are shown in FIGS. 20A and C, respectively. FIGS. 20D and E show the PA images by 805 nm and 680 nm wavelengths while they emitted together. Similar to FIG. 19, here the comparison between FIGS. 20C and 20D shows the effect on the generated image of adding another laser with mismatched modulation. The ultrasound image, FIG. 20D, shows the location of the tumor (highlighted). The photoacoustic images exhibited the vascularization area with much superior contrast.

Figure 21:
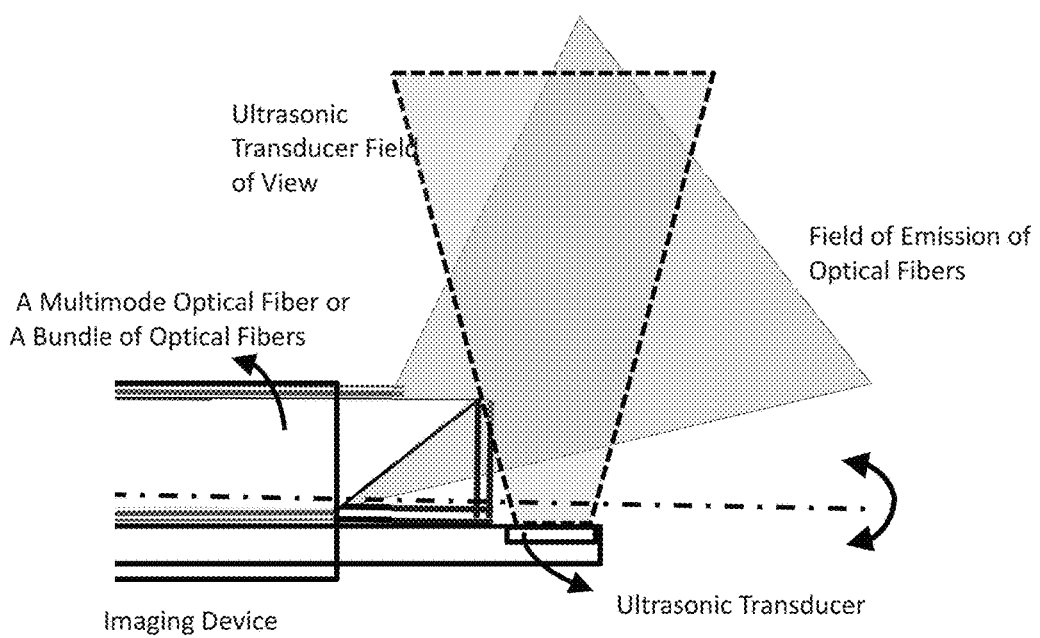
FIG. 21 shows a schematic example device for photoacoustic endoscopy imaging that can use mismatched coded excitation for fast imaging and characterization.

The same method can be employed for imaging or characterization by using a photoacoustic endoscopic imaging device (FIG. 21). The two mismatched coded excitations generated by up-sweep and down-sweep chirps as well as other described mismatched codes can be used for simultaneous detection of a photoacoustic signal with two or more wavelengths. It facilitates fast spectroscopic imaging or characterization.

Another example of use of mismatched coded excitations is in photothermal imaging (Tabatabaei, et al., J. Biomed. Opt., 2011; 16, 071402) and photothermal coherence tomography (Kaiplavil, et al. J. Biomed. Opt., 2014; 19, 026015). In these applications, laser beams with multiple wavelengths modulated with mismatched coded excitations can be employed to illuminate the subject. The thermal waves generated by laser illuminations can be detected by an infrared camera. In some embodiments, each chirped excitation may result in an image which is a photothermal image, and wherein the number of such photothermal images is the same as the number of laser excitation wavelengths. The photothermal images may be generated via a method in which the chirped excitations are delivered simultaneously. The photothermal images may be combined to generate a composite photothermal image. By using matched filtering, the outcome of each excitation (by each wavelength) can be distinguished. Therefore, similar to the photoacoustic application, the mismatched coded excitations can be used for simultaneous imaging and characterization.

Example 3

Use of Mismatched Codes for Crosstalk Cancelation

Figure 22:
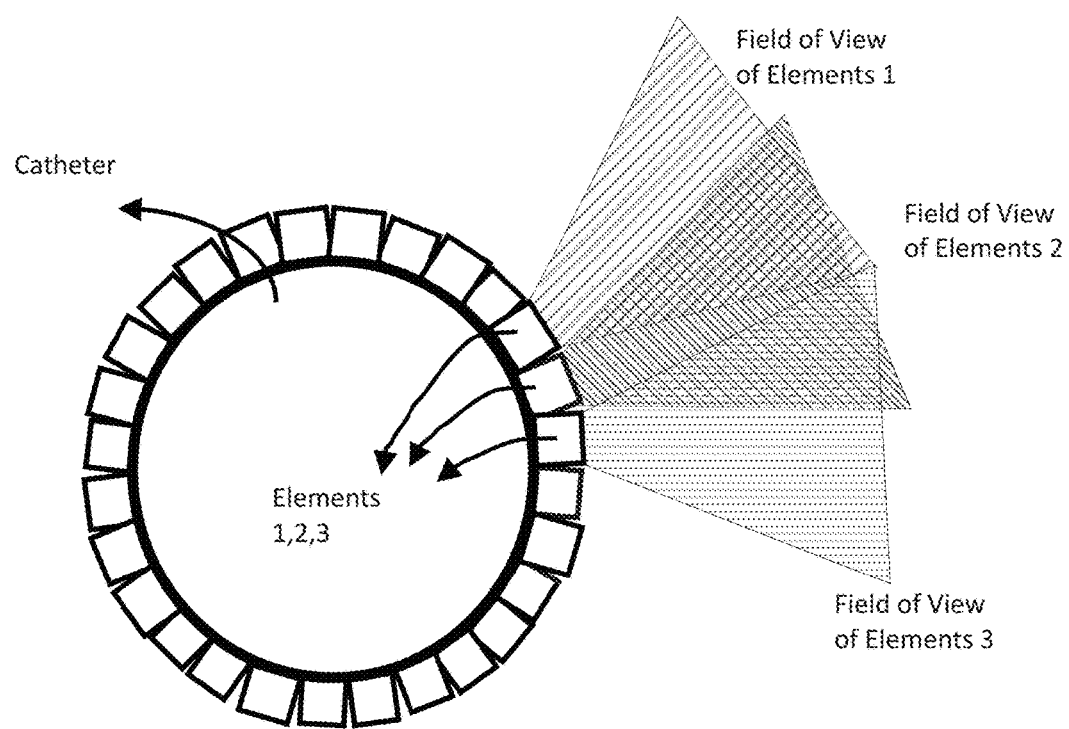
FIG. 22 shows an example of array elements located around a cylindrical catheter. Although the fields-of-view of most of the elements are separated, the crosstalk between the neighbouring elements is a major obstacle that prevents simultaneous signal transmission and detection. Mismatched coded excitation methods employed according to the teachings of the present disclosure may be useful in addressing this problem.

In some embodiments, mismatched coded excitations can be used to distinguish between the real signal and the crosstalk between array elements. An example is a radial array of ultrasonic piezoelectric elements located on the circumferential area of a cylindrical catheter. The piezoelectric elements may cover the complete or partial circumference of the convex area. Due to their diverging geometry, there could be a small overlap in the field of view of adjacent elements and no overlap between the field of view of elements farther away from each other (FIG. 22). However, even for elements located back to back, there could be a large amount of crosstalk transmitted electrically or by vibration through the catheter material itself. This issue is particularly important when the size of the catheter is small and insulation between elements is challenging. By using mismatched coded excitations, it is possible to assign each signal to a particular element. Therefore, this example embodiment enables the detection and cancelation of the crosstalk transmitted from other elements, and is a form a spatial encoding. This example embodiment facilitates simultaneous transmission from several elements without the limitation of the crosstalk interference between them.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES CITED

U.S. Patent Documents

Chiao, L. J. and, Thomas, R. Y., "Method and apparatus for ultrasonic synthetic transmit aperture imaging using orthogonal complementary codes". ultrasound U.S. Pat. No. 6,048,315; 2000.
Song, T. K., and, Jeong, Y. K., "Ultrasound imaging system and method based on simultaneous multiple transmit-focusing using weighted orthogonal chirp signals". ultrasound U.S. Pat. No. 7,066,886B2; 2006.

Other Publications

Behar, V., and, Adam, D., "Optimization of sparse synthetic transmit aperture imaging with coded excitation and frequency division". Ultrasonics. 2005; 43: 777-788.
Bredthauer, G. R. and, von Ramm, O. T., "Array design for ultrasound imaging with simultaneous beams". In IEEE Int. Symp. Biomedical Imaging; 2002; Washington D.C.
Chiao, R. Y., Thomas, L. J. and, Silverstein, S. D., "Sparse array imaging with spatially-encoded transmits". IEEE Ultrasonics Symposium. 1997; 2: 1679-1682.
Chiao, R. Y., and, Thomas, L. J., "Synthetic transmit aperture imaging using orthogonal Golay coded excitation". Proc. IEEE Ultrason. Symp. 2000; 1677-1680.
El-Khamy, S. E., Shaaban, S. E., and Thabet, E. A., "Efficient multiple access communications using multi-user chirp modulation signals". IEEE 4th International Conference on Spread-Spectrum Systems and Techniques (ISSSTA\'96). 1996; 1209-1213.
El-Khamy, S. E., Shaaban, S. E., and Thabet, E. A., "Frequency-hopped multi-user chirp modulation (FH/M-CM) for multipath fading channels". Proceedings of the Sixteenth National Radio Science Conference, NRSC '99. 1999: C6/1-C6/8. Golay, M., "Complementary Series," IRE Trans Inf Theory, Vols. IT-7:82-87, 1961.
Gran, F., and, Jensen, J. A., "Multi element synthetic aperture transmission using a frequency division approach". IEEE Ultrasonic Symposium. 2003; 1942-1946.
Gran, F., and, Jensen, J. A., "Spatio-temporal encoding using narrow-band linear frequency modulated signals in synthetic ultrasound imaging". SPIE Proc. Progress in Biomedical Optics and Imaging. 2005; 5750: 405-416.
Gran, F., and, Jensen, J. A., "Frequency division transmission imaging and synthetic aperture reconstruction". IEEE Trans. Ultrason. Ferroelectr. Freq. Control. 2006; 53(5): 900-911.
Griswold, M. A., Jakob, P. M., Chen, Q., Goldfarb, J. W., Manning, W. J., Edelman, R. R. and Sodickson, D. K., "Resolution enhancement in single-shot imaging using simultaneous acquisition of spatial harmonics (SMASH)". Magn Reson Med. 1999; 41: 1236-1245.
Hergum, T., Bjastad, T., Kristoffersen, K., and Torp, H., "Parallel beamforming using synthetic transmit beams". IEEE Trans. Ultrason. Ferroelectr. Freq. Control. 2007; 54(2): 271-280.
Jaffe, J. S., and, Cassereau, P. M., "Multibeam imaging using spatially variant insonification". J. Acoust. Soc. Am. 1988; 83(4): 1458-1464.
Jensen, J. A., Nikolov, S. I., Gammelmark, K. L., and Pedersen, M. H., "Synthetic Aperture Ultrasound Imaging". Ultrasonics J. 2006; 44: p. e5-e15.
Karaman, M., Li, P.-C., and O'Donnell, M., "Synthetic aperture imaging for small scale systems". IEEE Trans. Ultrason. Ferroelectr. Freq. Control. 1995; 42: 429-442.
Kiymik, M. K., Güler, I., Hasekioglub, O., Karaman, M., "Ultrasound imaging based on multiple beamforming with coded excitation". Signal Processing. 1997; 58: 107-113.
Lee, B. B., and, Furgason E. S., "Golay Codes for Simultaneous Multi-Mode Operation in Phased Arrays". Ultrasonics Symposium. 1982; 821-825.
Madore, B., White, P. J., Thomenius, K., and, Clement, T. "Accelerated focused ultrasound imaging". IEEE Trans. Ultrason. Ferroelectr. Freq. Control. 2009; 56(12): 2612-2623.
Mallart, R., Fink, M., "Improved imaging rate through simultaneous transmission of several ultrasound beams". Proc. SPIE 1730, New Developments in Ultrasonic Transducers and Transducer Systems. 1992; 120-130.
Mienkina, M. P., Friedrich, C. S., Gerhardt, N. C., Beckmann, M. F., Schiffner, M. F., Hofmann, M. R., Schmitz, G., "Multispectral Photoacoustic Coded Excitation imaging using unipolar Orthogonal Golay Codes," *Optics Express,* 2010; 18(9): 9076-9087.

Misaridis, T. and, Jensen J. A., "Space-time encoding for high frame rate ultrasound imaging". Ultrasonics. 2002; 40: 593-597.

Misaridis, T. and, Jensen J. A., "Use of modulated excitation signals in medical ultrasound. Part I: Basic concepts and expected benefits," IEEE Trans. Ultrason., Ferroelectr., Freq. Control., 2005: 52(2), 176-190.

Misaridis, T. and, Jensen J. A., "Use of modulated excitation signals in medical ultrasound, Part III: High frame rate imaging. IEEE Trans. Ultrason., Ferroelect., Freq. Contr. 2005: 52(2), 207-218.

Montaldo, G., Tanter, M., Bercoff, J., Benech, N., Fink, M., "Coherent Plane-Wave Compounding for Very High Frame Rate Ultrasonography and Transient Elastography". IEEE Trans. Ultrason. Ferr. Freq. Contr. 2009; 56(3): 489-506.

Purdy, D. S. "In orbit active array calibration for NASA's LightSAR". IEEE Proceedings of the Radar Conference. 1999; 172-176.

Sakamoto, T., and, Sato. T., "Code-Division Multiple Transmission for High-Speed UWB Radar Imaging With an Antenna Array". IEEE Transactions on Geoscience and Remote Sensing. 2009; 47(4): 1179-1186.

Shattuck, D. P., Weinshenker, M. D., Smith, S. W., and, von Ramm, O. T., "Explososcan: A parallel processing technique for high speed ultrasound imaging with linear phased arrays". J. Acoust. Soc. Am. 1984; 75(4): 1273-1282.

Shen, J., and Ebbini, E. S., "A new coded-excitation ultrasound imaging system—Part I: Basic principles". IEEE Trans. Ultrason. Ferroelectr. Freq. Control. 1996; 43: 131-140.

Silverstein, S. D., "Application of orthogonal codes to the calibration of active phased array antennas for communications satellites". IEEE Trans. Sig. Proc. 1997; 45(1): 206-218.

Szabo, T, Diagnostic Ultrasound Imaging: Inside out, Elsevier, 2004.

Tanter, M., and Fink, M. "Ultrafast Imaging in Biomedical Ultrasound". IEEE Trans. Ultrason. Ferroelectr. Freq. Control. 2014; 61(1): 102-119.

Telenkov, S., Alwi, R., Mandelis, A., and Worthington, A., "Frequency-domain photoacoustic phased array probe for biomedical imaging applications," Opt. Lett., vol. 36, no. 23, pp. 4560-4562, 2011.

von Ramm, O. T., Smith, S. W., and, Pavy, H. G., "High-speed ultrasound volumetric imaging system—Part II: Parallel processing and image display". IEEE Trans. Ultrason. Ferroelectr. Freq. Control. 1991; 38(2): 109-115.

Yang, M., and, Chakrabarti, C., "Design of orthogonal coded excitation for synthetic aperture imaging in ultrasound systems". IEEE International Symposium on Circuits and Systems (ISCAS). 2012; 113-116.

Zijlstra, W. G., Buursma, A. and van Assendelft, O. W., "Visible and Near Infrared Absorption Spectra of Human and Animal Haemoglobin: Determination and Application", Boston: VSP, 2000.

B. H. Kim, T. K. Song, "Multibeam Simultaneous Transmit Multizone (MB-STMZ) focusing method using modulated orthogonal codes for ultrasound imaging," Proc. SPIE, vol. 5373, p. 315-323, 2004.

J. S. Hwang, T. K. Song, "Ultrasound Imaging Apparatus and Method Using Golay Codes with Orthogonal Property". U.S. Pat. No. 6,547,733 B2, 15 Apr. 2003

C. E. Cook, "linear FM signal formats for beacon and communication systems," IEEE Trans. Aerosp. Electron. Syst., vol. AES-10, no. 4, pp. 471-478, 1974.\

N. Tabatabaei, A. Mandelis, and B. T. Amaechi, "Thermophotonics lock-in imaging of early demineralized and carious lesions in human teeth," J. Biomed. Opt., 2011; 16, 071402.

Kaiplavil, S., Mandelis, A. and Amaechi, B. T. "Truncated-correlation photothermal coherence tomography of artificially demineralized animal bones: two- and three-dimensional markers for mineral loss monitoring," J. Biomed. Opt., 2014; 19, 026015.

Therefore what is claimed is:

1. A method of performing encoded imaging using mismatched coded waveforms, the method comprising:
   a) transmitting coded imaging energy with one or more transmitter elements such that the coded imaging energy is directed onto an object to be imaged, wherein the coded imaging energy comprises a plurality of mismatched coded waveforms that are encoded with mismatched codes;
   b) receiving, with an array of receiver elements, secondary energy that is responsively generated, reflected or transmitted by the object, and thereby obtaining a set of received signals;
   c) calculating cross-correlations of the set of received signals with the plurality of mismatched coded waveforms, such that the cross-correlations isolate a contribution of each mismatched coded waveform to the set of received signals; and
   d) processing the cross-correlations to generate an image;
   wherein each coded mismatched waveform comprises a series of time divisions, each time division comprising a chirp;
   wherein the slope of each chirp, in each time division of each mismatched coded waveform, is unique; and
   wherein each mismatched coded waveform has an associated frequency range, such that the frequency ranges of the mismatched coded waveforms overlap at least in part.

2. The method according to claim 1 wherein the one or more transmitter elements are configured to generate coded optical excitation energy, and wherein the array of receiver elements are configured to receive acoustic energy, such that the image is a photoacoustic image.

3. The method according to claim 2 wherein the one or more transmitter elements and the array of receiver elements are components of a photoacoustic endoscope.

4. The method according to claim 1 wherein the one or more transmitter elements are a plurality of multiwavelength laser sources, and wherein the array of receiver elements are image elements (pixels) of an infrared camera, such that each chirped excitation results in an image which is a photothermal image, and wherein the number of such simultaneous photothermal images is the same as that of laser excitation wavelengths.

5. The method according to claim 1 wherein the frequency ranges of the mismatched coded waveforms are approximately equal.

6. The method according to claim 1 wherein the chirp of each time division of each mismatched coded waveform has an associated frequency range, such that the frequency ranges of the chirps within each mismatched coded waveform overlap at least in part.

7. The method according to claim 6 wherein the frequency ranges of the chirps within at least one mismatched coded waveform are approximately equal.

8. The method according to claim 7 wherein the duration of the time divisions within the at least one mismatched coded waveform are different.

9. The method according to claim 1 wherein the mismatched coded waveforms have equal time durations.

10. The method according to claim 1 wherein the one or more transmitter elements are a single transmitter element, and wherein the coded imaging energy is temporally coded by a series of mismatched coded waveforms.

11. The method according to claim 1 wherein the one or more transmitter elements are a plurality of transmitter elements, and wherein the coded imaging energy emitted from each transmitter element is temporally coded by a series of mismatched coded waveforms.

12. The method according to claim 1 wherein the one or more transmitter elements are an array of transmitter elements, and wherein the coded imaging energy emitted from each transmitter element is spatially coded by a unique mismatched coded waveform.

13. The method according to claim 1 wherein the one or more transmitter elements are an array of transmitter elements, and wherein the coded imaging energy emitted from each transmitter element is spatially and temporally coded, such that each transmitter element emits a unique series of mismatched coded waveforms.

14. The method according to claim 1 wherein the one or more transmitter elements are an array of transmitter elements, and wherein the array of transmitter elements and the array of receiver elements are elements of a transducer array, such that a first subset of elements of transducer array are configured as transmitters, and a second subset of elements of the transducer array are configured as receivers.

15. The method according to claim 14 wherein the image is a first image, the method further comprising
performing the following steps one or more times:
selecting different subsets of the elements of the transducer array for the array of transmitter elements and the array of receiver elements; and
repeating steps a) to d);
thereby obtaining one or more additional images.

16. The method according to claim 15 further where the first image and the one or more additional images are a set of low-resolution images, the method further comprising generating a high-resolution image from the low-resolution images.

17. The method according to claim 16 wherein the set of low-resolution images are obtained such that each element of the transducer array is configured as a transmitter element at least once.

18. A method of performing encoded imaging, the method comprising:
a) transmitting coded imaging energy with one or more transmitter elements such that the coded imaging energy is directed onto an object to be imaged, wherein the coded imaging energy comprises a plurality of mismatched coded waveforms that are encoded with mismatched codes;
b) receiving, with an array of receiver elements, secondary energy that is responsively generated, reflected or transmitted by the object, and thereby obtaining a set of received signals;
c) calculating cross-correlations of the set of received signals with the plurality of mismatched coded waveforms, such that the cross-correlations isolate a contribution of each mismatched coded waveform to the set of received signals; and
d) processing the cross-correlations to generate an image;
wherein the plurality of mismatched coded waveforms comprise two or more concatenated mismatched coded waveforms, wherein each concatenated mismatched coded waveform is formed by concatenating two or more phase-coded waveforms having different frequencies.

19. The method according to claim 18 wherein the one or more transmitter elements are configured to generate coded optical excitation energy, and wherein the array of receiver elements are configured to receive acoustic energy, such that the image is a photoacoustic image.

20. The method according to claim 19 wherein the one or more transmitter elements and the array of receiver elements are components of a photoacoustic endoscope.

21. The method according to claim 18 wherein the one or more transmitter elements are a plurality of multiwavelength laser sources, and wherein the array of receiver elements are image elements of an infrared camera, such that each chirped excitation results in an image which is a photothermal image, and wherein the number of such simultaneous photothermal images is the same as that of laser excitation wavelengths.

22. The method according to claim 18 wherein the phase-codes waveforms are Golay coded waveforms;
wherein the plurality of mismatched coded waveforms comprise a plurality of pairs of coded waveforms, each pair comprising a Golay coded waveform and a second Golay coded waveform that is complementary to the first Golay coded waveform;
the method further comprising adding the cross-correlations obtained for each pair of coded waveforms prior to processing the cross-correlations to generate the image.

23. The method according to claim 22 wherein the plurality of mismatched coded waveforms have equal durations.

24. The method according to claim 22 wherein each concatenated mismatched coded waveform is formed by concatenating the phase-coded waveforms having the same code but different frequencies.

25. The method according to claim 22 wherein one pair of the mismatched coded waveforms is a conventional Golay coded waveform, and wherein the one or more concatenated mismatched coded waveforms are generated by concatenating two Golay coded waveforms having half the bit length of the conventional Golay coded waveform, wherein each of the two Golay coded waveforms have different frequencies.

26. The method according to claim 25 wherein the different frequencies of the two Golay coded waveforms are selected such that their average frequency is approximately equal to the frequency of the conventional Golay coded waveform.

27. A method of performing encoded imaging, the method comprising:
a) transmitting coded imaging energy with one or more transmitter elements such that the coded imaging energy is directed onto an object to be imaged, wherein the coded imaging energy comprises a plurality of mismatched coded waveforms that are encoded with mismatched codes;
b) receiving, with an array of receiver elements, secondary energy that is responsively generated, reflected or transmitted by the object, and thereby obtaining a set of received signals;
c) calculating cross-correlations of the set of received signals with the plurality of mismatched coded waveforms, such that the cross-correlations isolate a contribution of each mismatched coded waveform to the set of received signals; and d) processing the cross-correlations to generate an image;

wherein the plurality of mismatched coded waveforms are two or more phase-coded waveforms, wherein each bit of each phase-coded waveform is chirped;

wherein the chirps within a given phase-coded waveform are equal; and wherein the chirps among different phased-coded waveforms are different; and wherein each phase-coded waveform has an associated frequency range, such that the frequency ranges of the phase-coded waveforms overlap at least in part.

28. The method according to claim 27 wherein the one or more transmitter elements are configured to generate coded optical excitation energy, and wherein the array of receiver elements are configured to receive acoustic energy, such that the image is a photoacoustic image.

29. The method according to claim 28 wherein the one or more transmitter elements and the array of receiver elements are components of a photoacoustic endoscope.

30. The method according to claim 28 wherein the one or more transmitter elements are a plurality of multiwavelength laser sources, and wherein the array of receiver elements are image elements of an infrared camera, such that such that each chirped excitation results in an image which is a photothermal image, and wherein the number of such simultaneous photothermal images is the same as that of laser excitation wavelengths.

31. The method according to claim 27 wherein the phase-coded waveforms are Golay-coded waveforms;

wherein the plurality of mismatched coded waveforms comprise a plurality of pairs of coded waveforms, each pair comprising a Golay coded waveform and a second Golay coded waveform that is complementary to the first Golay coded waveform;

the method further comprising adding the cross-correlations obtained for each pair of coded waveforms prior to processing the cross-correlations to generate the image.

32. The method according to claim 27 wherein the frequency ranges of the phase-coded waveforms are approximately equal.

33. The method according to claim 27 wherein the phase-coded waveforms have equal time durations.

34. A method of performing encoded imaging using mismatched coded waveforms, the method comprising:

a) transmitting coded imaging energy with one or more transmitter elements such that the coded imaging energy is directed onto an object to be imaged, wherein the coded imaging energy comprises a plurality of mismatched coded waveforms that are encoded with mismatched codes, wherein the one or more transmitter elements are an array of transmitter elements, and wherein the coded imaging energy emitted from each transmitter element is spatially and temporally coded, such that each transmitter element emits a unique series of mismatched coded waveforms;

b) receiving, with an array of receiver elements, secondary energy that is responsively generated, reflected or transmitted by the object, and thereby obtaining a set of received signals, wherein the array of transmitter elements and the array of receiver elements are elements of a transducer array, such that a first subset of elements of transducer array are configured as transmitters, and a second subset of elements of the transducer array are configured as receivers;

c) calculating cross-correlations of the set of received signals with the plurality of mismatched coded waveforms, such that the cross-correlations isolate a contribution of each mismatched coded waveform to the set of received signals; and d) processing the cross-correlations to generate a first image; and e) performing the following steps one or more times:
    selecting different subsets of the elements of the transducer array for the array of transmitter elements and the array of receiver elements; and
    repeating steps a) to d);
thereby obtaining one or more additional images.

35. The method according to claim 34 wherein the one or more transmitter elements are configured to generate coded optical excitation energy, and wherein the array of receiver elements are configured to receive acoustic energy, such that the image is a photoacoustic image.

36. The method according to claim 35 wherein the one or more transmitter elements and the array of receiver elements are components of a photoacoustic endoscope.

37. The method according to claim 34 wherein the one or more transmitter elements are a plurality of multiwavelength laser sources, and wherein the array of receiver elements are image elements of an infrared camera, such that each chirped excitation results in an image which is a photothermal image, and wherein the number of such simultaneous photothermal images is the same as that of laser excitation wavelengths.

38. The method according to claim 34 further where the first image and the one or more additional images are a set of low-resolution images, the method further comprising generating a high-resolution image from the low-resolution images.

39. The method according to claim 38 wherein the set of low-resolution images are obtained such that each element of the transducer array is configured as a transmitter element at least once.

40. A method of performing encoded imaging using mismatched coded waveforms, the method comprising:

a) transmitting coded optical imaging energy with one or more optical transmitter elements such that the coded optical imaging energy is directed onto an object to be imaged, wherein the coded optical imaging energy comprises a plurality of mismatched coded waveforms that are encoded with mismatched codes;

b) receiving, with an array of ultrasound receiver elements, secondary energy that is responsively generated by the object, and thereby obtaining a set of received signals;

c) calculating cross-correlations of the set of received signals with the plurality of mismatched coded waveforms, such that the cross-correlations isolate a contribution of each mismatched coded waveform to the set of received signals; and d) processing the cross-correlations to generate an image;

wherein the coded mismatched waveforms comprise frequency chirps having equal and opposite slopes.

* * * * *